(12) United States Patent
Schlenoff

(10) Patent No.: US 8,206,816 B2
(45) Date of Patent: Jun. 26, 2012

(54) POLYMER MECHANICAL DAMPING COMPOSITES AND METHODS OF PRODUCTION

(75) Inventor: Joseph B. Schlenoff, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 643 days.

(21) Appl. No.: 12/439,647

(22) PCT Filed: Aug. 29, 2007

(86) PCT No.: PCT/US2007/077146
§ 371 (c)(1),
(2), (4) Date: Mar. 2, 2009

(87) PCT Pub. No.: WO2008/027989
PCT Pub. Date: Mar. 6, 2008

(65) Prior Publication Data
US 2010/0009148 A1    Jan. 14, 2010

Related U.S. Application Data

(60) Provisional application No. 60/823,842, filed on Aug. 29, 2006.

(51) Int. Cl.
*B32B 5/00* (2006.01)
*C08J 5/20* (2006.01)
*C08J 5/00* (2006.01)
*B29C 43/00* (2006.01)

(52) U.S. Cl. ..... 428/220; 428/500; 521/27; 264/331.11; 264/320

(58) Field of Classification Search ............... 428/220, 428/500; 264/331.11, 320; 521/27
See application file for complete search history.

(56) References Cited

U.S. PATENT DOCUMENTS

| | | | |
|---|---|---|---|
| 3,276,598 A | 10/1966 | Michaels et al. | |
| 3,546,142 A | 12/1970 | Michaels et al. | |
| 3,558,744 A | 1/1971 | Michaels et al. | |
| 3,565,973 A | 2/1971 | Michaels | |
| 4,539,373 A | 9/1985 | Mani et al. | |
| 6,660,367 B1 | 12/2003 | Yang et al. | |
| 6,905,875 B2 | 6/2005 | Yu et al. | |
| 7,101,947 B2 | 9/2006 | Schlenoff et al. | |
| 7,105,229 B2 | 9/2006 | Anderson | |
| 7,223,327 B2 | 5/2007 | Schlenoff et al. | |
| 7,238,536 B1 | 7/2007 | Schlenoff | |
| 7,387,824 B2 | 6/2008 | Tamagawa et al. | |
| 2004/0265603 A1 | 12/2004 | Schlenoff | |
| 2005/0176620 A1* | 8/2005 | Prestwich et al. | ................ 514/2 |
| 2005/0282925 A1 | 12/2005 | Schlenoff et al. | |
| 2005/0287111 A1 | 12/2005 | Schlenoff et al. | |
| 2006/0051532 A1* | 3/2006 | Tamagawa et al. | ........ 428/32.39 |
| 2006/0065529 A1 | 3/2006 | Schlenoff et al. | |

(Continued)

OTHER PUBLICATIONS

Allen, Norman S., "Polymer Photochemistry", Photochemistry, 2007, vol. 36, pp. 232-297.

(Continued)

*Primary Examiner* — Michael M Bernshteyn
(74) *Attorney, Agent, or Firm* — Armstrong Teasdale LLP

(57) ABSTRACT

An article comprising a polyelectrolyte complex, the polyelectrolyte complex comprising an intermolecular blend of a predominantly positively-charged polyelectrolyte and a predominantly negatively charged polyelectrolyte and being free of salt crystals having a size greater than about 1 micrometer and free of voids having a size greater than about 100 nm, the article having no transverse dimension less than about 10,000 nm.

25 Claims, 10 Drawing Sheets

U.S. PATENT DOCUMENTS

2006/0073333 A1* 4/2006 Anderson .................. 428/402.2
2007/0259452 A1 11/2007 Schlenoff
2007/0265174 A1 11/2007 Schlenoff

OTHER PUBLICATIONS

Biggerstaff et al., "Damping Performance of Cocured Graphite/Epoxy Composite Laminates with Embedded Damping Materials", Journal of Composite Materials, 1999, vol. 33, No. 15, pp. 1457-1469.

Dai et al., "Controlling the Permeability of Multilayered Polyelectrolyte Films through Derivatization, Cross-Linking, and Hydrolysis", Langmuir, 2001, vol. 17, No. 3, pp. 931-937.

Dubas et al., "Swelling and Smoothing of Polyelectrolyte Multilayers by Salt", Langmuir, 2001, vol. 17,pp. 7725-7727.

Graul et al., "Capillaries Modified by Polyelectrolyte Multilayers for Electrophoretic Separations", Analytical Chemistry, 1999, vol. 71, No. 18, pp. 4007-4013.

Holmlin et al., "Zwitterionic SAMs that Resist Nonspecific Adsorption of Protein from Aqueous Buffer", Langmuir, 2001, vol. 17, No. 9, pp. 2841-2850.

Iatridis et al., "The Viscoelastic Behavior of the Non-Degenerate Human Lumbar Nucleus Pulposus in Shear", J. Biomechanics, 1997, vol. 30, No. 10, pp. 1005-1013.

Iatridis et al., "Shear Mechanical Properties of Human Lumbar Annulus Fibrosus", Journal of Orthopaedic Research, 1999, vol. 17, No. 5, pp. 732-737.

Jaber et al., "Mechanical Properties of Reversibly Cross-Linked Ultrathin Polyelectrolyte Complexes", Journal of American Chemical Society, 2006, vol. 128, pp. 2940-2947.

Kozlovskaya et al., "Hydrogen-Bonded Polymer Capsules Formed by Layer-by-Layer Self-Assembly", Macromolecules, 2003, vol. 36, pp. 8590-8592.

Lim et al., "Microencapsulated Islets as Bioartificial Endocrine Pancreas", Science, New Series, 1980, vol. 210, No. 4472, pp. 908-910.

Losche et al., "Detailed Structure of Molecularly Thin Polyelectrolyte Multilayer Films on Solid Substrates as Revealed by Neutron Reflectometry", Macromolecules, 1998, vol. 31, No. 25, pp. 8893-8906.

Michaels, Alan S., "Polyelectrolyte Complexes", Industrial & Engineering Chemistry, 1965, vol. 57, No. 10, pp. 32-40.

Rosidian et al., "Ionic Self-Assembly of Ultrahard ZrO2/Polymer Nanocomposite Thin Films", Advanced Materials, 1998, vol. 10, No. 14, pp. 1087-1091.

Smets, G., "Photocross-Linkable Polymers", Journal of Macromolecular Science Chemistry, 1984, A21(13 & 14), pp. 1695-1703.

Strehmel, Veronika, "Epoxies: Structures, Photoinduced Cross-Linking, Network Properties, and Applications", Handbook of Photochemistry and Photobiology, 2003, Chapter 1, pp. 1-110.

Sui et al., "Phase Separations in pH-Responsive Polyelectrolyte Multilayers: Charge Extrusion versus Charge Expulsion", Langmuir, 2004, vol. 20, No. 14, pp. 6026-6031.

Timpe, Hans-Joachim, "Polymer Photochemistry and Photo-Cross-Linking", Desk Reference of Functional Polymers: Syntheses and Applications, 1997, pp. 273-291.

Poly(Ethylene Glycol) Chemistry: Biotechnical and Biomedical Applications (Table of Contents only), Edited by Milton J. Harris, 1992, Plenum Press, New York, New York, 13 pages.

R. Reese Handbook of Antibiotics (Table of Contents and Preface only), Third Edition, 2000, 3 pages, Lippincott Williams and Wilkins, Philadelphia, Pennsylvania.

International Search Report, PCT/US2007/77146, dated Mar. 7, 2008, 2 pages.

Written Opinion of the International Searching Authority, PCT/US2007/77146, dated Mar. 7, 2008, 8 pages.

* cited by examiner

POLYMER MECHANICAL DAMPING COMPOSITES AND METHODS OF PRODUCTION

CROSS-REFERENCE TO RELATED APPLICATIONS

This application claims priority from International Application PCT/US2007/077146, filed on Aug. 29, 2007 and published as WO 2008/027989 and from U.S. provisional application Ser. No. 60/823,842, filed on Aug. 29, 2006, the contents of which are incorporated by reference in their entirety.

STATEMENT REGARDING FEDERALLY SPONSORED RESEARCH OR DEVELOPMENT

This invention was made with Government support under Grant No. DMR 0309441 awarded by the National Science Foundation. The Government has certain rights in the invention.

FIELD OF THE INVENTION

The present invention relates to methods and materials to form compacted articles comprising a polyelectrolyte complex and uses of said articles.

BACKGROUND OF THE INVENTION

Vibrations in mechanical systems can have adverse consequences, such as fatigue, failure, and noise. Vibration suppression is achieved by passive or active methods. While active methods reduce vibrations in real time by making use of sensors and actuators, passive methods exploit the inherent ability of viscoelastic materials such as polymers to absorb and dissipate vibration energy. The Maxwell model, which comprises an elastic element (spring) and a viscous element (dashpot) in series, illustrates damping: for high frequency vibrations the Maxwell model predicts almost perfect elastic behavior, i.e., minimal energy dissipation, as the motion of the dashpot becomes negligible. For low or moderate frequencies the time scales of the viscoelastic relaxation and vibration are comparable, and they interfere destructively with one another, allowing for more efficient energy dissipation and damping.

Mechanical damping materials remove energy from a system. Motions to be damped can be periodic and regular (e.g., sine wave, square wave) or they can be irregular. Often a single mechanical event must be damped. Such an event is termed a shock, and the mechanical damping is termed shock absorption. Most damping measurements apply a periodic deformation to the article being tested, but it is also possible to assess the damping characteristics of a material from a single shock.

The Young's modulus, E, (also known as elastic modulus, modulus of elasticity, or tensile modulus) is a measure of the stiffness of a material. E is the ratio between the tensile stress, $\sigma$, divided by the tensile strain, e. E is typically measured on a tensile apparatus which elongates a material and reports the stress needed to produce a certain strain. Alternatively, a sample is compressed and the required stress for a needed deformation is measured. E may be measured under static, or quasi-static, conditions, where the stress does not vary with time. Alternatively, the modulus can be measured under dynamic or time-varying conditions where a material may exhibit properties of elasticity and viscous flow (viscoelasticity) in which case the modulus depends on frequency of deformation and a complex modulus, E*, is defined, where $E^*=E_1+iE_2$, where $E_1$ is the storage modulus, which is a measure of energy stored on a deformation cycle, and $E_2$ is the loss modulus, which is a measure of the energy lost on a cycle.

The shear modulus, G, (also referred to as the modulus of rigidity) of a material, measured under dynamic or time-varying conditions, is the ratio of the shear stress to the shear strain. The shear modulus is typically measured with a parallel-plate rheometer. If the shear rate changes, G depends on the frequency at which the shear changes. Therefore, a complex shear modulus is defined as $G^*=G_1+iG_2$, where $G_1$ is the storage modulus, which is a measure of energy stored on a deformation cycle, and $G_2$ is the loss modulus, which is a measure of the energy lost on a cycle. For isotropic materials, E=3G for small deformations. For the present purposes, a material with low E is termed "soft" while a material with low G is termed "flowable."

The ratio $E_1/E_2$ or $G_1/G_2$ is equal to $\tan(\Delta)$, the ratio of energy lost to energy stored in one cycle. $\tan(\Delta)$ is called the loss factor and is a measure of damping efficiency, with greater damping indicated by higher $\tan(\Delta)$.

Damping or shock-absorbing properties are not determined from static measurements. Damping properties are ascertained by time varying or periodic deformation of the sample. Thus, a soft material (low E) is not necessarily a good candidate for damping. Furthermore, a material that is effective for damping over a certain frequency range may not be effective for damping over another frequency range. Therefore, in reporting a complex modulus (E* or G*), a frequency or frequency range is preferably specified.

Recent studies have evaluated the static mechanical properties of polyelectrolyte multilayers, which are ultrathin films of complexed polyelectrolytes. See, for example, Jaber, J. A. and Schlenoff, J. B., J. Am. Chem. Soc. 128, 2940-2947 (2006). Polyelectrolyte multilayers are intermolecular blends of positively and negatively charged polyelectrolyte, wherein each layer of polyelectrolyte added to a growing film has an opportunity to complex efficiently and completely with the existing material, excluding the maximum amount of water. The elastic modulus of these films ranges from kPa to MPa. However, these films are far too thin (a few micrometers or less) to be used for mechanical components in most systems. Furthermore, the dynamic mechanical properties of molecularly blended complexes of positive and negative polyelectrolytes have not been evaluated. Polyelectrolyte complexes are prepared in a straightforward manner by mixing solutions of positive and negative polyelectrolytes.

The maximum amplitude of mechanical damping of an article generally depends on the physical dimensions of the article. Thus, there is a need to prepare articles with dimensions in the millimeter to centimeter scale to absorb the shock of mechanical vibrations on the millimeter scale. While a polyelectrolyte complex is easily prepared by mixing solutions of individual polyelectrolytes well, the precipitate is gelatinous and difficult to process. The dried complexes, for example, are generally infusible and therefore cannot be injection molded or reformed into articles under elevated temperatures. See Michales, A. S., J. Industrial Engin. Chem. 57, 32-40 (1965).

Polyelectrolyte complexes have been proposed as tissue engineering scaffolding (e.g., see Lim and Sun, Science, 210: 908-910 (1980) and Yu et al., U.S. Pat. No. 6,905,875). The purpose of a tissue engineering scaffold is to support and maintain growing cells. Thus, these scaffolds are usually soft and porous and, therefore, not well suited for use as a compressive mechanical support. A tissue engineering scaffold is typically designed, prepared and employed without designing or expecting a particular damping property.

SUMMARY OF THE INVENTION

Among the various aspects of the present invention may be noted the provision of an article that may be used to dampen the vibrations between two abutting surfaces, and to methods for preparing such an article. In one embodiment, the article is a 3-dimensional object comprising compacted polyelectrolyte complex adapted for mechanical damping operations, which may be used for mechanical damping over the frequency range $0.1\text{-}10^6$ Hz. In another embodiment, a method is provided for producing articles comprising compact blends of positive and negative polyelectrolytes, said method comprising the centrifugal compaction of a suspension of polyelectrolyte complex into a form or shape in the presence of salt. The article may be introduced into a cavity by pressure injection through a needle of centrifugally compacted polyelectrolyte complex in the presence of salt. Accordingly, the invention is further directed to a method for replacing the nucleus pulposis material of an intervertebral disk, the method comprising separating the vertebrae, removing the from 0 to 100% of the existing nucleus pulposis, and injecting compacted polyelectrolyte complex through a needle into the space occupied by the nucleus pulposis.

Briefly, therefore, one aspect of the present invention is an article comprising a polyelectrolyte complex. The polyelectrolyte complex comprises an intermolecular blend of a predominantly positively-charged polyelectrolyte and a predominantly negatively charged polyelectrolyte. The polyelectrolyte complex is free of salt crystals having a size greater than about 1 micrometer and free of voids having a size greater than about 100 nm. The article has no transverse dimension that is less than about 10,000 nm.

Another aspect of the present invention is a method for preparing an article comprising a polyelectrolyte complex. The method comprises combining the predominantly positively-charged polyelectrolyte and the predominantly negatively charged polyelectrolyte in a solution having a salt of at least 0.1 M to form a polyelectrolyte complex having a doping level ratio between about 0.01 and about 0.50. In addition, a mechanical force is applied to compact the polyelectrolyte complex and thereby form an article comprising the compacted polyelectrolyte complex.

Another aspect of the present invention is a method for modifying a complex shear modulus of an article comprising a polyelectrolyte complex, the polyelectrolyte complex being an intermolecular blend of a predominantly positively-charged polyelectrolyte and a predominantly negatively charged polyelectrolyte and containing at least about 30 wt. % water at 25° C. in the presence of an aqueous 0.15 M salt solution. The method comprises contacting the article with a first solution comprising a salt to change the doping level ratio from a first salt doping level ratio to a second doping level ratio, whereby changing the doping level ratio in the polyelectrolyte complex changes the complex shear modulus of the polyelectrolyte complex from a first complex shear modulus to a second complex shear modulus.

Another aspect of the present invention is a method of damping vibrations between two abutting surfaces over a frequency range between about 0.1 Hz and about 10,000 Hz. The method comprises positioning an polyelectrolyte complex article between the two surfaces, the polyelectrolyte complex comprising an intermolecular blend of a predominantly positively charged polyelectrolyte and a predominantly negatively charged polyelectrolyte.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE EMBODIMENTS OF THE INVENTION

Figure 1:
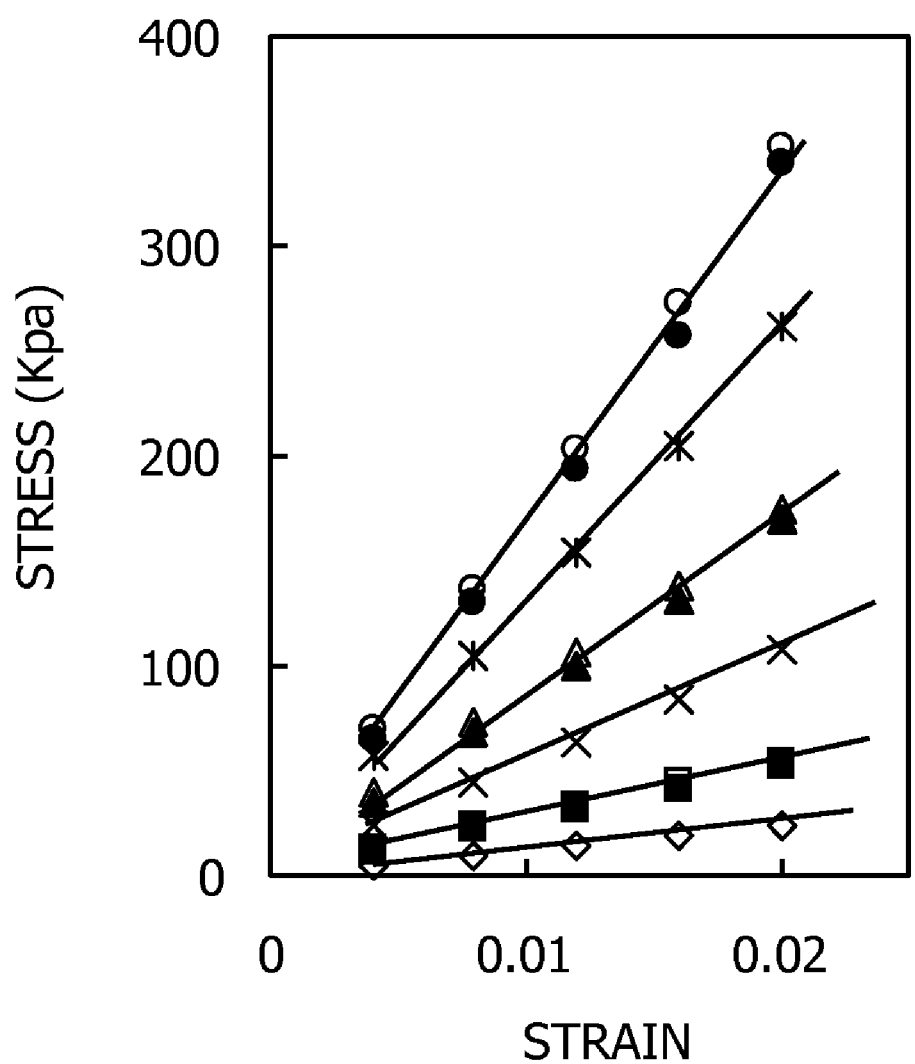
FIG. 1 is graph showing the stress-strain behavior of a polyelectrolyte complex after conditioning at several ionic strengths. The data in the graph were obtained according to the method of Example 1.

One aspect of the invention is an article capable of damping vibrations. The article comprises a polymer, in particular, a polymer known as a "polyelectrolyte" that comprises multiple electrolytic groups that dissociate in aqueous solutions, making the polymer charged. The article of the present invention comprises a polyelectrolyte complex, that is, an intermolecular blend of a predominantly positively-charged polyelectrolyte and a predominantly negatively-charged polyelectrolyte. The polyelectrolyte complex is preferably compacted, such as by centrifugation or pressure, in a manner that increases the density of the polyelectrolyte complex to a value substantially greater than that which may be obtained by conventional intermixing, precipitation and centrifugation methods. Moreover, the compacted article may be prepared to have dimensions typically on the order of millimeters to centimeters, which is also substantially greater than that achievable by conventional multilayering and intermixing methods.

In accordance with one aspect of the present invention, it has been discovered that the static and dynamic mechanical properties of a polyelectrolyte complex may be controlled and varied by changing the concentration of salt ions within the bulk of the article. In particular, it has been discovered that increasing the salt concentration within the bulk of the polyelectrolyte complex decreases the elastic modulus, rendering the material softer. Furthermore, is has been discovered that the complex shear modulus may be controlled by the addition of salt, causing the article to be more flowable, and injectable under shear conditions. Conversely, decreasing the salt concentration with the bulk of the polyelectrolyte complex increases the complex shear modulus, rendering it a stiffer material. Accordingly, the dynamic mechanical properties of an article comprising the polyelectrolyte complex may be initially controlled by controlling the salt concentration during the preparation of the polyelectrolyte complex and then altered by increasing or decreasing the salt concentration of the solution contacting the article after preparation. Thus, for example, a flowable compacted article may be prepared in the presence of high salt concentration, and then injected into a cavity. Once the flowable article is in the cavity, a concentration gradient may be applied by contacting the compacted article with a solution having a lower salt concentration, which thereby causes salt located in the bulk of the article to leach out into the solution, making the compacted article less flowable, thereby causing the article to become a permanent feature within the cavity. If desired, a salt concentration gradient may be reapplied by contacting the compacted article with a solution having a high salt concentration, which thereby causes the bulk of the material to increase in salt concentration, thereby making the material flowable again, which would facilitate its removal from the cavity.

In general, the polyelectrolyte complex is formed by combining a predominantly negatively charged polyelectrolyte and a predominantly positively charged polyelectrolyte to form an article. In a preferred embodiment, the article is prepared by combining separate solutions, each containing one of the polyelectrolytes; in this embodiment, at least one solution comprises a predominantly positively-charged polyelectrolyte, and at least one solution comprises a predominantly negatively-charged polyelectrolyte. Either or both of these solutions may comprise additives, such as salt ions. The formation of a polyelectrolyte complex, Pol$^+$Pol$^-$, by mixing individual solutions of the polyelectrolytes in their respective salt forms, Pol$^+$A$^-$ and Pol$^-$M$^+$, may be represented by the following equation:

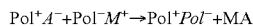

where M$^+$ is a salt cation, such as sodium, and A is a salt anion such as chloride. Pol$^-$ and Pol$^+$ represent repeat units on predominantly negatively charged and predominantly positively charged polyelectrolytes, respectively. According to the equation, the process of complexation releases salt ions into external solution, which are then part of the salt solution concentration.

Separate solutions containing the polyelectrolytes are preferably combined in a manner that allows the positively-charged polyelectrolyte and the negatively-charged polyelectrolyte to intermix. Intermixing the respective polyelectrolytes causes the in situ formation of a polyelectrolyte complex comprising an intermolecular blend of the positively-charged polyelectrolyte and the negatively-charged polyelectrolyte. Preferably, at least one of the solutions comprises salt ions, such that salt ions also intermix with and become part of the polyelectrolyte complex. The resulting polyelectrolyte complex may simply be allowed to precipitate and settle to the bottom of the container. The supernatant is, in a preferred embodiment, separated to the extent possible from the polyelectrolyte complex.

Individual polyelectrolyte solutions that are mixed may themselves comprise mixtures of polyelectrolytes. For example, a solution may comprise two positive polyelectrolytes with two distinct chemical compositions. When the mixture of positive polyelectrolytes is mixed with the negative polyelectrolyte solutions the resulting complex will incorporate a blend of the two positive polyelectrolytes. Such a strategy is described for example in Z. Sui, J. B. Schlenoff, Langmuir vol 18, p 8263 (2003).

The precipitated polyelectrolyte complex is preferably compacted. In one embodiment, compacting may be accomplished by centrifugation, such that the polyelectrolyte complex is compacted into a plug of material inside the centrifuge vessel. In a preferred embodiment, salt is present during compaction.

Polyelectrolytes for Complexes

The charged polymers (i.e., polyelectrolytes) used to form the complexes are water and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative, and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly(diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive repeat units and negative repeat units distributed throughout the polymer in a random, alternating, or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic. An example of a zwitterionic repeat unit is 3-[2-(acrylamido)-ethyldimethyl ammonio]propane sulfonate, AEDAPS. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units.

The charges on a polyelectrolyte may be derived directly from the monomer units, or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly (ether ether ketone) (SPEEK), poly(ethylenesulfonic acid), poly(methacryloxyethylsulfonic acid), their salts, and copolymers thereof; polycarboxylates such as poly (acrylic acid) (PAA) and poly(methacrylic acid), polyphosphates, and polyphosphonates.

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH) and polyethyleneimine (PEI); polysulfoniums, and polyphosphoniums.

Exemplary polyelectrolyte repeat units, both positively charged and negatively charged, are shown in Table I.

TABLE I

| Polyelectrolyte Repeat Units | |
|---|---|
| Name | Structure |
| diallyldimethylammonium (PDADMA) | |
| styrenesulfonic acid (PSS) | |
| N-methyl-2-vinyl pyridinium (PM2VP) | |
| N-methyl-4-vinylpyridinium (PM4VP) | |
| N-octyl-4-vinylpyridinium (PNO4VP) | |

TABLE I-continued

Polyelectrolyte Repeat Units

| Name | Structure |
|---|---|
| N-methyl-2-vinyl pyridinium-co-ethyleneoxide (PM2VP-co-PEO) | 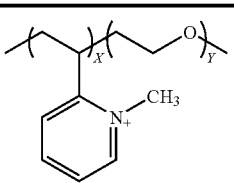<br>X and Y denote proportions of repeat units |
| acrylic acid (PAA) | 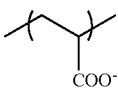 |
| allylamine (PAH) | 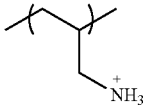 |
| ethyleneimine (PEI) | 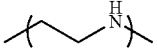 |

Further examples of oppositely-charged polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule comprises a protonated sub-unit (e.g., protonated amines). Some negatively charged biomacromolecules comprise a deprotonated sub-unit (e.g., deprotonated carboxylates or phosphates). Examples of biomacromolecules which may be charged for use in accordance with the present invention include proteins, polypeptides, enzymes, DNA, RNA, heparin, alginic acid, chondroitin sulfate, chitosan, chitosan sulfate, cellulose sulfate, polysaccharides, dextran sulfate, carrageenin, sulfonated lignin, and carboxymethylcellulose.

Natural, or biological, polyelectrolytes typically exhibit greater complexity in their structure than synthetic polyelectrolytes. For example, proteins may comprise any combination of about 2 dozen amino acid building blocks. Polymeric nucleic acids such as DNA and RNA may also comprise many different monomer repeat units. The sign and magnitude of the charge on proteins depends on the solution pH, as the charge on proteins is carried by weak acids, such as carboxylates (—COOH), or weak bases, such as primary, secondary, and tertiary amines. Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte typically comprises about 0.01% to about 40% by weight of a polyelectrolyte solution, and preferably about 1% to about 20% by weight.

Many of the foregoing polymers/polyelectrolytes, such as PDADMA and PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention. Block polyelectrolytes, wherein a macromolecule comprises at least one block of charged repeat units, are also suitable. The number of blocks may be 2 to 5. Preferably, the number of blocks is 2 or 3. If the number of blocks is 3 the block arrangement is preferably ABA.

Many of the foregoing polyelectrolytes have a very low toxicity. In fact, poly(diallyldimethylammonium chloride), poly(2-acrylamido-2-methyl-1-propane sulfonic acid) and their copolymers are used in the personal care industry, e.g., in shampoos. Also, because the polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Since some solvents are known to be incompatible with some plastic materials, preferred solvents for depositing polyelectrolyte complex thin films on plastics are water and alcohols. Preferred solvents are aqueous.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), and protonated polyamines, such as, poly(allylamine hydrochloride) and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonic acid), poly(diallyldimethylammonium chloride), poly(N-methylvinylpyridinium) and poly(ethyleneimine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

The charged polyelectrolyte may be a synthetic copolymer comprising pH sensitive repeat units, pH insensitive repeat units, or a combination of pH sensitive repeat units and pH insensitive repeat units. pH insensitive repeat units maintain the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

It is understood that the term "pH sensitive," as applied to functional groups, refers to functional groups that exhibit differing degrees of ionization over the working pH range of the experiment, while pH insensitive refers to functional groups that maintain the same charge (either positive or negative) over the working pH range of the experiment.

For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte at the surface of, or within, a polyelectrolyte complex.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly (acrylic acids), poly(methacrylic acids), poly(carboxylic acids), and copolymers thereof. Additional preferred polyelectrolytes comprise protonatable nitrogens, such as poly (pyridines), poly(imidazoles), poly(piperidines), and poly (amines) bearing primary, secondary or tertiary amine groups, such as poly(allylamine).

To avoid disruption and possible decomposition of the polyelectrolyte complex, polyelectrolytes comprising pH sensitive repeat units additionally comprise pH insensitive charged functionality on the same molecule. In one embodiment, the pH-insensitive repeat unit is a positively charged repeat unit selected from the group consisting of repeat units containing a quaternary nitrogen atom, a sulfonium ($S^+$) atom, or a phosphonium atom. Thus, for example, the quaternary nitrogen may be part of a quaternary ammonium moiety ($—N^+R_aR_bR_c$ wherein $R_a$, $R_b$, and $R_c$ are independently alkyl, aryl, or mixed alkyl and aryl), a pyridinium moiety, a bipyridinium moiety or an imidazolium moiety, the sulfonium atom may be part of a sulfonium moiety ($—S^+R_dR_e$ wherein $R_d$ and $R_e$ are independently alkyl, aryl, or mixed alkyl and aryl) and the phosphonium atom may be part of a phosphonium moiety ($—P^+R_fR_gR_h$ wherein $R_f$, $R_g$, and $R_h$ are independently alkyl, aryl, or mixed alkyl and aryl). In another embodiment, the pH-insensitive repeat unit is a negatively charged repeat unit selected from the group consisting of repeat units containing a sulfonate ($—SO_3^-$), a phosphate ($—OPO_3^-$), or a sulfate ($—SO_4^-$).

Exemplary negatively charged pH insensitive charged repeat units include styrenesulfonic acid, 2-acrylamido-2-methyl-1-propane sulfonic acid, sulfonated lignin, ethylenesulfonic acid, methacryloxyethylsulfonic acid, sulfonated ether ether ketone, phosphate. Preferred pH insensitive negatively charged polyelectrolytes include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly (ether ether ketone) (SPEEK), sulfonated lignin, poly(ethylenesulfonic acid), poly(methacryloxyethylsulfonic acid), their salts, and copolymers thereof.

Exemplary positively charged pH insensitive repeat units include diallyldimethylammonium, vinylbenzyltrimethylammonium, ionenes, acryloxyethyltrimethyl ammonium chloride, methacryloxy(2-hydroxy)propyltrimethyl ammonium, N-methylvinylpyridinium, other N-alkylvinyl pyridiniums, a N-aryl vinyl pyridinium, alkyl- or aryl imidazolium, sulfonium, or phosphonium. Preferred pH insensitive positively-charged polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly (N-methylvinylpyridinium) (PMVP), other poly(N-alkylvinylpyridines), and copolymers thereof.

For illustrative purposes, certain of the pH insensitive positively-charged moieties are illustrated below:

Pyridinium having the structure:

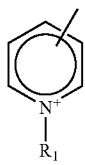

wherein $R_1$ is optionally substituted alkyl, aryl, alkaryl, alkoxy or heterocyclo. Preferably, $R_1$ is alkyl or aryl, and still more preferably $R_1$ is methyl.

Imidazolium having the structure:

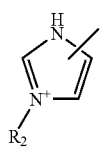

wherein $R_2$ is optionally substituted alkyl, aryl, alkaryl, alkoxy or heterocyclo. Preferably, $R_2$ is alkyl or aryl, and still more preferably $R_2$ is methyl.

Bipyridinium having the structure:

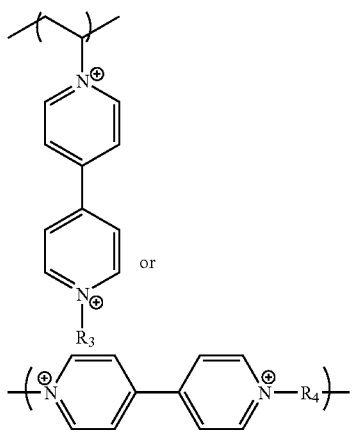

wherein $R_3$ and $R_4$ are optionally substituted alkyl, aryl, alkaryl, alkoxy or heterocyclo. Preferably, $R_3$ and $R_4$ are alkyl or aryl, and still more preferably $R_3$ is methyl.

The pH insensitive polyelectrolyte may comprise a repeat unit that contains protonatable functionality, wherein the functionality has a pKa outside the range of experimental use. For example, poly(ethyleneimine) has protonatable amine functionality with pKa in the range 8-10, and is thus fully charged (protonated) if the experimental conditions do not surpass a pH of about 7.

Preferably, the pH-insensitive groups constitute about 10 mol % to about 90 mol % of the repeat units of the polyelectrolyte, more preferably from about 20 mol % to about 80 mol %. Preferably, the pH-sensitive groups constitute about 30 mol % to about 70 mol % of the repeat units of the polyelectrolyte. The ratio of pH-sensitive to pH-insensitive charged repeat units comprising a polyelectrolyte molecule, or a blend of polyelectrolyte molecules, is important. Too few pH-insensitive charged repeat units may be insufficient to hold the polyelectrolyte complex together when the pH is changed. Too many charged pH-insensitive units will not allow the charge of the complex to change sufficiently to trap and release proteins. The preferred ratio of pH sensitive functional group to pH insensitive charged functional group enables control of surface and/or bulk charge without leading to disruption of the thin polyelectrolyte complex film. Thus ratios of pH sensitive functional group to pH insensitive charged functional group are preferably in the range 1:10 to 10:1, and more preferably in the range 2:10 to 10:2. Similarly, the total percentage of pH sensitive functional group is preferably between 5% and 95%.

Optionally, the polyelectrolytes comprise an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, ethylene oxide, and vinyl caprolactam. The structures of these uncharged repeat units are shown in Table II.

TABLE II

Neutral Repeat Units

| Name | Structure |
| --- | --- |
| Acrylamide | 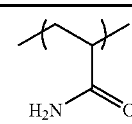 |
| Vinylpyrrolidone | 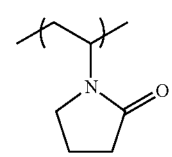 |
| Ethylene oxide | 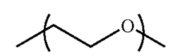 |
| Vinylcaprolactam | 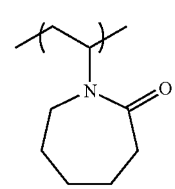 |

Protein adsorption is driven by the net influence of various interdependent interactions between and within surfaces and biopolymer. Possible protein-polyelectrolyte interactions can arise from 1) van der Waals forces 2) dipolar or hydrogen bonds 3) electrostatic forces 4) hydrophobic effects. Given the apparent range and strength of electrostatic forces, it is generally accepted that the surface charge plays a major role in adsorption. However, proteins are remarkably tenacious adsorbers, due to the other interaction mechanisms at their disposal. It is an object of this invention to show how surfaces may be selected to encourage or discourage the adsorption of proteins to centrifugally compacted polyelectrolyte complexes when they are used in vivo. Protein adsorption may be discouraged by copolymerizing with vinyl repeat units having hydrophilic groups, vinyl repeat units having zwitterionic groups, and hydrophilic repeat units.

It is also known by those skilled in the art that zwitterionic functional groups are also effective at resisting the adsorption of biomacromolecules, such as proteins (e.g. see Holmlin et al. *Langmuir,* 17, 2841 (2001)). In one embodiment of this invention, centrifugally compacted polyelectrolyte complex articles also comprise zwitterionic functional groups. It has been found that polymers comprising zwitterionic functional groups alone do not form polyelectrolyte complexes if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. For control of bulk and surface charge of polyelectrolyte complexes, polyelectrolytes comprising zwitterionic groups also comprise pH sensitive units. These pH sensitive units are preferably acrylic acids, methacrylic acids, carboxylic acids, and copolymers thereof, and protonatable nitrogens, such as pyridines, imidazoles, piperidines, and primary, secondary, or tertiary amine groups, such as allylamine. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio]propane sulfonate) (PAEDAPS) and poly(N-propane sulfonate-2-vinyl pyridine) (P2PSVP). The structures of these zwitterions are shown in Table III.

TABLE III

Zwitterionic Repeat Units

| Name | Structure |
| --- | --- |
| 3-[2-(acrylamido)-ethyldimethyl ammonio] propane sulfonate (AEDAPS) | 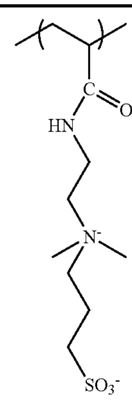 |
| N-propane sulfonate-2-vinyl pyridine (2PSVP) | 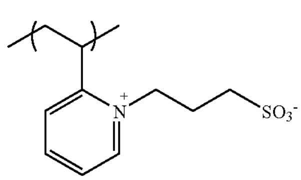 |

It has been disclosed by Graul and Schlenoff (*Anal. Chem.,* 71, 4007 (1999)) that polyelectrolyte films prepared by the multilayering method are able to control the adsorption of protein. The adsorption of basic proteins (that is, those with a positive net charge at the operating pH) is preferably minimized by terminating the polyelectrolyte complex film with a positive charge, which repels the positive proteins. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) Chemistry: Biotechnical and Biomedical Applications*, Plenum Press, New York, 1992). Yang and Sundberg (U.S. Pat. No. 6,660,367) disclose materials comprising ethylene glycol units that are effective at resisting the adsorption of hydrophilic proteins in microfluidic devices. In the present invention, copolymers of poly (ethylene oxide), PEO, or poly(ethylene glycol), PEG, are preferred materials for surface modification. The ethylene oxide (or ethylene glycol) repeat units are preferably present as blocks within a block copolymer. Preferably, the block copolymer also comprises blocks of charged repeat units, allowing the material to be incorporated into a polyelectrolyte complex. Sufficient ethylene oxide repeat units are required to promote resistance to protein adsorption, but too many ethylene oxide units do not allow polyelectrolyte complexes to associate. Therefore, the preferred ratio of charged to neutral blocks in a polyelectrolyte complex from 10:1 to 1:4, and a more preferred ratio is 5:1 to 1:2.

In some applications, the compacted article comprises polyelectrolyte that renders the article biocompatible. Preferred polyelectrolyte film coatings for biocompatibility comprise fluorinated polymers, preferably fluorinated polyelectrolytes. See, for example, U.S. Pub. No. 2005/0287111, the entire contents of which are hereby incorporated in their entirety. Fluorinated polyelectrolytes are preferably copolymers, or copolyelectrolytes, comprising fluorinated and non-fluorinated repeat units. Said repeat units may be disposed in a random or block fashion on the backbone of said copolyelectrolytes. Preferred fluorinated copolyelectrolytes comprise charged non-fluorinated with noncharged fluorinated repeat units, or charged fluorinated with noncharged nonfluorinated repeat units. Other preferred fluorinated polyelectrolytes comprise charged fluorinated repeat units with charged nonfluorinated repeat units. Fluorinated copolyelectrolytes are preferably made by post-polymerization reactions on polymers, such as alkylation, or by polymerization of fluorinated monomers or mixtures of fluorinated monomers. Mole percentages of fluorinated repeat units on fluorinated copolyelectrolytes are preferably from 10% to 95%, and more preferably from 20% to 95%.

For illustrative purposes, certain fluorinated moieties are shown as vinyl repeat units:

Vinyl Polymer Repeat Unit

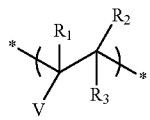

wherein $R_1$, $R_2$, and $R_3$ are each independently: —$(CH_2)_m$H or —$(CH_xF_{2-x})_n$F and m and n are independently 0 to 12, x is 0, 1, or 2 and V is a group selected from among the following:

fluorinated hydrocarbons having the structure:

—$(CH_2)_p(CF_2)_q$F,

—$(CH_2)_p(CF_2)_q$COOH,

—$(CH_2)_p(CF_2)_qOPO_3^-$,

—$(CH_2)_p(CF_2)_qSO_3^-$,

—$(CH_2)_p(CF_2)_qOSO_3^-$,

—$O(CH_2)_p(CF_2)_qF$,

—$O(CH_2)_p(CF_2)_qSO_3^-$ and wherein p is 0 to 6 and q is 1 to 21;

fluorinated amides having the structure:

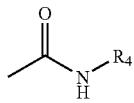

wherein $R_4$ is —$(CH_2)_p(CF_2)_qF$,

—$(CH_2)_p(CF_2)_qCOOH$,

—$(CH_2)_p(CF_2)_qOPO_3^-$,

—$(CH_2)_p(CF_2)_qSO_3^-$,

—$(CH_2)_p(CF_2)_qOSO_3^-$ and wherein p is 0 to 6 and q is 1 to 21;

fluorinated esters having the structure:

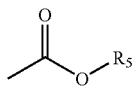

wherein $R_5$ is —$(CH_2)_p(CF_2)_qF$,

—$(CH_2)_p(CF_2)_qCOOH$,

—$(CH_2)_p(CF_2)_qOPO_3^-$,

—$(CH_2)_p(CF_2)_qSO_3^-$,

—$(CH_2)_p(CF_2)_qOSO_3^-$ and wherein p is 0 to 6 and q is 1 to 21;

fluorinated phenyl groups having the structure:

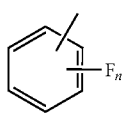

wherein n is 2 to 5; or

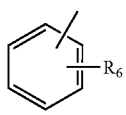

wherein $R_6$ is —$(CH_2)_p(CF_2)_qF$ or —$O(CH_2)_p(CF_2)_qF$ and wherein p is 0 to 6 and q is 1 to 21;

fluorinated pyridiniums having the structure:

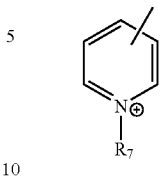

wherein $R_7$ is —$(CH_2)_p(CF_2)_qF$ and wherein p is 0 to and q is 1 to 21;

fluorinated imidazoliums having the structure:

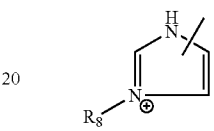

wherein $R_8$ is —$(CH_2)_p(CF_2)_qF$ and wherein p is 0 to and q is 1 to 21;

fluorinated quaternary nitrogens having the structure:

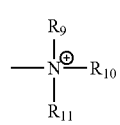

wherein $R_9$, $R_{10}$, and $R_{11}$ are each independently —$(CH_2)_p(CF_2)_qF$ and wherein p is 0 to 6 and q is 1 to 21 or -aryl$F_z$ wherein z is 2 to 8;

fluorinated sulfoniums having the structure:

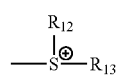

wherein $R_{12}$ and $R_{13}$ are each independently $(CH_2)_p(CF_2)_qF$ wherein p is 0 to 6 and q is 1 to 21 or -aryl$F_z$ wherein z is 2 to 8; and fluorinated phosphoniums having the structure:

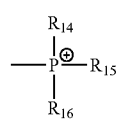

wherein $R_{14}$, $R_{15}$, and $R_{16}$ are each independently —$(CH_2)_p(CF_2)_qF$ wherein p is 0 to 6 and q is 1 to 21 or -aryl$F_z$ where z=2 to 8.

For illustrative purposes, certain of these moieties are shown as allyl repeat units (e.g., PDADMA):

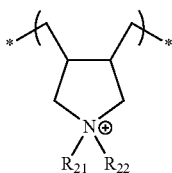

wherein $R_{21}$ and $R_{22}$ are —$(CH_2)_p(CF_2)_qF$ wherein p and q are independently selected for $R_{21}$ and $R_{22}$, and p is 0 to 6 and q is 1 to 21.

Table IV shows the structures of fluorinated polyelectrolytes that may be present in the compacted polyelectrolyte complex articles of the present invention.

TABLE IV

Fluorinated Polyelectrolyte Repeat Units

| Name | Structure |
|---|---|
| 4-vinyl-trideca-fluoro-octyl pyridinium iodide-co-4-vinyl pyridine (PFPVP) | Where M is a mole fraction typically from about 0.1 to about 1.0, preferably from about 0.3 to about 0.8 |
| NAFION | Where X, Y, and X denote molar proportions; X may be from about 6 to about 10 parts, Y may be about 1 part and Z may be from about 1 to about 3 parts |

In one preferred embodiment, a small amount of chemical crosslinking is introduced into the compacted polyelectrolyte complex for stability. Chemical crosslinking is preferably accomplished by including difunctional monomers in the polyelectrolytes comprising the complex. For example, a divinyl repeat unit added to the polymerization reaction will be incorporated into two polyelectrolyte chains, giving a crosslink at the connection point. Alternatively, a compacted article may be treated with a difunctional crosslinking agent, such as $XCH_2$-ϕ-$CH_2X$, where X is a halogen (Cl, Br, or I) and ϕ is a phenyl group. The phenyl group may be replaced by another aromatic or aliphatic moiety, and easily-diplaceable groups, such as toluene sulfonate, may replace the halogen. A preferred crosslinking agent is a dihalogenated compound, such as an aromatic or aliphatic dibromide, which is able to alkylate residual unalkylated units on two adjoining polyelectrolyte chains.

Another preferred method of crosslinking a compacted polyelectrolyte complex is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (Macromolecules, 36, 8590 (2003)) is by the addition of a carbodiimide, which activates chemical crosslinking. The level of crosslinking is preferably 0.01% to 50%, and more preferably 0.1% to 10%. Without being bound to a particular theory, it is thought that crosslinking within the ranges given herein increases the ability of the compacted polyelectrolyte complex article to remember its shape after a deformation event.

Another method of crosslinking a compacted polyelectrolyte complex is by photocrosslinking. Photocrosslinking may be achieved by the light-induced decomposition or transformation of functional groups that form part of the polymer molecules. See, for example, Strehmel, Veronika, "Epoxies: Structures, Photoinduced Cross-linking, Network Properties, and Applications"; Handbook of Photochemistry and Photobiology (2003), 2, 1-110. See also Allen, Norman S., "Polymer photochemistry", Photochemistry (2004), 35, 206-271; Timpe, Hans-Joachim "Polymer photochemistry and photocrosslinking" Desk Reference of Functional Polymers (1997), 273-291, and Smets, G., "Photocrosslinkable polymers", Journal of Macromolecular Science, Chemistry (1984), A21(13-14), 1695-703. Alternatively, photocrosslinking of a polyelectrolyte complex may be accomplished by infusing the compacted polyelectrolyte complex with a small photoactive molecule, then exposing the polyelectrolyte complex to light.

Crosslinking between polyelectrolyte pairs is not an essential requirement for the compacted article of the present invention to exhibit shape memory after a significant deformation event. In fact, each ion pair between a positively-charged repeat unit and a negatively-charged repeat unit acts as an electrostatic cross-link that enhances the compacted article's ability to remember its shape after deformation. Since electrostatic cross-link between ion pairs can approach nearly 100% of the charged repeat units (in the absence of or in low concentration of salt), the compacted polyelectrolyte complex of the present invention is able to reform into its original shape after a tensile deformation event that stretches the article at least about twice its original dimension, preferably at least about three times its original dimension, even more preferably at least about four times its original dimension.

When the bulk of the compacted article comprises a significant salt concentration, salt ions disrupt electrostatic cross-linking by associating with charged repeat units. Therefore, salt works like lubricating agent allowing polyelectrolytes to slip past each other during a deformation event and thus enhancing the flowability the compacted articles.

Salt Content

In one embodiment, the compacted polyelectrolyte complex of the present invention may be prepared in a manner that incorporates a significant salt ionic concentration within the bulk of the compacted article. The salt ionic concentration may be achieved by preparing and/or compacting the article in solutions comprising salt ions. Stated differently, the polyelectrolyte complex is doped with salt ions to increase the ionic strength of the polyelectrolyte complex. The extent of doping and the identity of the salt ions may be varied to advantageously control the elastic and dynamic mechanical properties of the polyelectrolyte complex. Sources of salt ions for doping include the polyelectrolyte material, which is often available in its ionic form and from added salt. Salts include soluble, ionic compounds that dissociate in solution to stable ions (e.g., sodium chloride). A salt may comprise organic ions, inorganic ions, or a combination of organic and inorganic ions. A salt may be included in the polyelectrolyte solutions to control the processability, elastic modulus, flowability, injectability, and swelling of the compacted polyelectrolyte complex article. For physiological applications, ions selected to control mechanical properties are preferably of minimal toxicity. Anions and/or cations with charge greater than one are preferred for inducing greater flowability at lower concentration.

A wide variety of salt ions may be added to the compacted article of the present invention to influence the article's mechanical properties. In general, the salt may comprise any cation selected from among the alkali metal cations, alkaline earth metal cations, transition metal cations, semi-metallic cations, and organic cations such as amines. The salt(s) may comprise a mixture of two or more of any of these cations. Among the alkali metal cations, lithium, sodium, potassium, and rubidium may be incorporated into the compacted article, with sodium and potassium being particularly preferred. In certain physiological applications, the choice of alkali metal cations may be limited to sodium or potassium ions. Among the alkaline earth metal cations, magnesium, calcium, strontium, and barium may be incorporated into the compacted article. Calcium and magnesium cations are particularly preferred, and for physiological applications, the choice of alkaline earth metal cations may be limited to calcium and magnesium. A wide variety of transition metals may be incorporated into the compacted article including scandium, yttrium, titanium zirconium, vanadium, niobium, chromium, molybdenum, manganese, iron, ruthenium, cobalt, rhodium, nickel, palladium, platinum, copper, silver, gold, and zinc. In certain physiological application, the choice of transition metal cations may be limited to zinc, silver, iron, and copper. Semi-metallic cations that may be incorporated into the compacted articles include aluminum, indium, tin, lead, and bismuth. Organic cations that may be included include ammonium, primary, secondary, tertiary, and quaternary amines comprising alkyl groups having from one to four carbon atoms. Primary amines, secondary amines, and tertiary amines are protonated to achieve positive charge and are thus pH sensitive. Accordingly, they are preferably used under acidic conditions. Exemplary primary amines, secondary amines, and tertiary amines are protonated forms of methylamine, dimethylamine, trimethyl amine, ethylamine, diethylamine, and triethylamine among others. Quaternary amines are pH insensitive groups. Exemplary quaternary amines include tetramethylamine, tetraethylamine, tetrapropylamine, among others. In one embodiment, the amine is a linear polyamine such as ethylene diamine, diethylene triamine, dipropylene triamine, triethylene tetraamine, tripropylene tetraamine, tetraethylene pentaamine, tetrapropylene pentaamine, spermine, or spermidine.

The anion may be selected from among halide anions, oxoanions, and organic anions. A combination of anions may be incorporated into the compacted article. Halide ions that may be incorporated into the compacted article include fluoride, chloride, bromide, and iodide. Advantageously, any of these halides may be incorporated into compacted articles for use in physiological applications. In one preferred embodiment, the halide anion is chloride ion. In another preferred embodiment, the halide anion is chloride ion with a relatively low concentration of fluoride ion. Incorporation of a low concentration of fluoride ion is advantageous when the compacted article is used in or near bone, such as in dental implants or in intervertebral space. Oxoanions that may be incorporated into the compacted article include sulfonate, sulfate, sulfite, phosphate, phosphite, phosphonate, pyrophosphate, hypochlorite, chlorite, chlorate, perchlorate, iodate, periodate, bromate, borate, carbonate, nitrate, nitrate, aluminate, and manganate, among others. Organic anions that may be incorporated into the compacted article include carboxylates, such as citrate, lactate, acetate, benzoate, formate, malate, malonate, fumarate, oxalate, propionate, butyrate, tartrate, and valerate, phthalate, among others. Hydrophobic anions, such as those with a high hydrocarbon to charge ratio, are preferred for enhancing doping and flowability. Preferred organic anions for physiological applications include citrate and lactate.

In view of the above cations and anions, a wide variety of salts may be incorporated into the compacted articles of the present invention. Preferably, the salts are soluble in aqueous solution at a concentration at least sufficient to incorporate ions into the compacted article to an extent sufficient to achieve desired elastic and shear moduli. In some embodiments, however, a relatively insoluble salt may be incorporated to impart some other desired characteristic, for example, biocompatibility. In these embodiments, the insoluble salt may be present in the polyelectrolyte solutions in a relatively low concentration and may be combined with another salt having high solubility. For example, calcium citrate has relatively low solubility (about 0.01 M in 0.1 M HCl). In certain applications, it may be desirable to include calcium citrate, but its limited solubility hinders its ability to substantially affect the article's elastic modulus or flowability. Therefore, the polyelectrolyte solution may further comprise a highly soluble salt, such as sodium chloride, for example, that will become incorporated in a high enough concentration to achieve the desired elastic modulus or flowability.

Particularly preferred salts include chloride salts, citrate salts, and phosphate salts. Preferred chloride salts include sodium chloride, potassium chloride, magnesium chloride, calcium chloride, and aluminum chloride. Preferred citrate salts include trisodium citrate, disodium hydrogencitrate, sodium dihydrogencitrate, tripotassium citrate, dipotassium hydrogencitrate, potassium dihydrogencitrate, magnesium citrate, and calcium citrate. Preferred phosphate salts include trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, and magnesium phosphate.

As stated above, incorporation of a salt into the bulk of the compacted polyelectrolyte complex affects the elastic and dynamic mechanical properties of the article comprising the complex, such as, for example, the elastic and complex shear modulus. It has been observed that increasing the salt concentration decreases the article's G*, meaning that as the salt concentration increases, the article becomes more flowable and injectable. Conversely, decreasing the salt concentration increases G*, making the article harder and more likely to hold a shape. It has also been observed that incorporation of cations and anions having multiple valences (i.e., an absolute charge of two or greater) for a given concentration decreases elastic modulus and G* to a greater extent than does incorporation of singly charged cations and anions. For example, incorporating calcium chloride into the compacted article by preparing and/or compacting it in a solution having a calcium chloride concentration of 0.2 M decreases the article's elastic and shear moduli to a greater extent than does preparing/compacting the article in the presence of solution comprising sodium chloride at a concentration of 0.2 M. Stated another way, salts comprising high valence ions may be incorporated in lower concentrations than salts comprising singly charged ions to achieve the same modulus reducing effect.

In general, salt ions may be incorporated within the bulk of the article both during preparation of the polyelectrolyte complex and during compaction. Typically, the concentration of salt ions within the bulk of the article equilibrates with the salt ion concentration of the solution in which the polyelectrolyte complex is prepared or the solution in which the article is compacted. Equilibration may be fairly rapid, with durations typically on the order of between about 1 minute and about 30 minutes per millimeter thickness of the compacted polyelectrolyte complex article. In general, the salt ions located within the bulk of the polyelectrolyte complex associate with (i.e., form ionic bonds to) charged repeat units located in the positively charged and negatively charged polyelectrolytes. The salt ion concentration within the bulk of the compacted article comprising polyelectrolyte complex may be quantified in terms of a doping level ratio, determined by dividing the sum of the ionic charge provided by salt ions by the sum of charge provided by the polymer repeat units. This ratio may be expressed in terms of a doping level percentage by multiplying the doping level ratio by 100. The doping level ratio is typically between about 0.01 to 0.50, preferably between about 0.02 and about 0.2. Stated in terms of a percentage, the doping level is preferably between about 1% and about 50%, more preferably between about 2% and about 20%. To illustrate a doping level ratio calculation, suppose that a simple polyelectrolyte complex comprises a blend of one positively charged polyelectrolyte having 100 positively charged repeat units and one negatively charged polyelectrolyte having 100 negatively charged repeat units. Such a polyelectrolyte complex therefore has a total charge provided by the charged repeat units of 200. This polyelectrolyte complex may be doped with salt ions which become associated with at least some of the charged repeat units. For example, if 10 sodium ions are associated with 10 negatively charged repeat units and 10 chloride ions are associated with 10 positively charged repeat units, the sum of charges provided by the salt ions is 20. The doping level ratio is calculated by dividing the sum of charges of the salt ions by the sum of charges from the repeat units, i.e., 20/200=0.1, or 10%, stated as a doping level percentage. By way of further example, if 5 calcium ions (2+) are associated with 10 negatively charged repeat units and 10 chloride ions are associated with 10 positively charged repeat units, the sum of charges provided by the salt ions is 20 (=5×2 for the calcium+10 for the chloride) and the doping level ratio is 20/200=0.1, or 10%, stated as a doping level percentage. To achieve these doping levels, the polyelectrolyte complex may be prepared or compacted in solutions having salt ion concentrations between about 0.01 M and about 4 M, preferably between about 0.1 M and about 3 M, even more preferably between about 0.15 M and about 1 M. The salt concentration employed during preparation and compaction includes those ions liberated from the polyelectrolytes by complexation.

In general, the complex shear modulus of a compacted polyelectrolyte complex of the present invention may vary between about 1 kPa and about 400 MPa, such as between about 1 MPa and about 20 MPa, between frequencies of about 0.1 Hz and 10,000 Hz. The complex shear modulus of the compacted polyelectrolyte complex depends, at least in part, on three factors: the chemical composition of polyelectrolytes, the salt ions, and the concentration of salt within the bulk of the polyelectrolyte complex. For example, G* of a compacted article comprising comprising poly(styrene sulfonate) (PSS) and poly(diallyldimethylammonium) (PDADMA) decreases between about 2 MPa and about 0.1 MPa per 0.1 M increase in ionic concentration within the bulk of the article at about 10 Hz. In another example, G* of a compacted article comprising polymethacrylic acid and PDADMA decreases with increasing sodium chloride as shown in the following Table V. In Table V, the values of G* at various frequencies for the nucleus pulposus of the human lumbar intervertebral disc are shown for comparison. Advantageously, the viscoelastic behavior of an intervertebral disc of the pulposus may be reproduced by a compacted poly (methacrylic acid)/poly(diallyldimethylammonium) (PMAA/PDADMA) polyelectrolyte complex article.

TABLE V

Comparison of Complex Shear Modulus Behavior of Nucleus Pulposus and Polyelectrolyte Complex

| Material | W (rad/s) | \|G*\| | Δ (deg) |
|---|---|---|---|
| Nucleus pulposus[1] | 1 | 7.40 ± 11.6 | 23 ± 5 |
|  | 10 | 11.30 ± 17.9 | 24 ± 5 |
|  | 100 | 19.8 ± 31.4 | 30 ± 6 |
| PMAA/PDAD 0.15M | 1 | 3.2 | 38 |
|  | 10 | 7.5 | 30 |
|  | 100 | 15.2 | 25 |
| PMAA/PDAD 0.00M | 1 | 7.3 | 32 |
|  | 10 | 15.0 | 27 |
|  | 100 | 27.2 | 23 |

[1](from J. S. Iatridis et al, J. Biomechanics, 30, p. 1005-1012 (1997)).

In one embodiment, the complex shear modulus of a compacted article comprising polyelectrolyte complex prepared in a solution comprising between about 0.1 M and about 0.5 M sodium chloride may, after equilibration, be between about 0.1 MPa and about 5 MPa over a frequency range of 0.1 to 1000 Hz. A compacted article having a complex shear modulus within this range may be loaded into a cavity, such as an intevertebral disk space, through a cannula. Preferably, the polyelectrolyte complex is prepared in a solution having a higher sodium chloride concentration, such as between about 0.15 M and about 0.30 M, more preferably about 0.25 M, to yield an article having a G* near the lower end of the stated range, which yields a more flowable and more easily injected article. Potassium chloride achieves a greater decrease in G* for a given concentration than does sodium chloride. Accordingly, preferred potassium chloride salt concentrations are between about 0.1 M and about 0.4 M, such as between about 0.15 M and about 0.3 M.

Water Content

The polymeric constituents of polyelectrolyte complexes are highly charged and hydrophilic, and although the individual charged units are less hydrophilic when ion paired within the article, each ion pair is solvated. Accordingly, when in contact with water at room temperature (25° C.), a compacted polyelectrolyte complex may comprise anywhere from about 5 wt. % to about 90 wt. % water, typically between about 10 wt. % and about 70 wt. % water at room temperature. An exemplary compacted article, in the form of an ultrathin multilayer, comprising poly(diallyldimethylammonium) and poly(styrene sulfonate), for example, may comprise between about 50 and about 70 wt % water. See Dubas and Schlenoff, "Swelling and Smoothing in Polyelectrolyte Multilayers", Langmuir 2001, 17, 7725.

Water content within the bulk of the compacted article is thought to enhance the article's damping ability to a point. Polyelectrolyte complexes prepared by precipitation and centrifugation at relatively low centrifugation rates (e.g. 5,000 rpm), however, may contain too much water. For example, a PDADMA/PSS complex precipitated and centrifuged at 5,000 rpm on a 20 cm radius rotor arm for 30 min contained more than 90 wt % water and it had a shear modulus which was less than desirable and the sample could neither be formed into a shape nor loaded into a rheometer. In general, therefore, it is preferred that the water content be less than about 85 wt. %, more preferably below about 80 wt. %, even more preferably below about 70 wt. % (when the polyelectrolyte complex is in contact with aqueous solutions, for example a 0.15 M salt solution, at room temperature (25° C.)). To attain the advantages of enhanced damping, it is preferred that the water content be at least about 10 wt. %, preferably at least about 20 wt., even more preferably at least about 30 wt. % (when the polyelectrolyte complex is in contact with aqueous solutions, for example a 0.15 M salt solution, at room temperature (25° C.).

Additional Additives

Further additives that may be incorporated into the polyelectrolyte complex include inorganic materials such as metallic oxide particles (e.g., silicon dioxide, aluminum oxide, titanium dioxide, iron oxide, zirconium oxide, and vanadium oxide) and clay minerals (e.g., hectorite, kaolin, laponite, montmorillonite). For example, nanoparticles of zirconium oxide added to a polyelectrolyte solution or complex solution tend to improve the abrasion resistance of the article. See Rosidian et al., *Ionic Self-assembly of Ultra Hard $ZrO_2$/polymernanocomposite Films,* Adv. Mater. 10, 1087-1091. High aspect ratio fillers are preferred for stiffening a compacted article at a relatively low fill loading. Preferred high aspect ratio additives include needle-like clay minerals, such as attapulgite, and carbon-based fibers such as carbon fiber or single or multiwalled carbon nanotubes.

Methods of Preparation

One method for preparing articles in the form of a film or other body of a polyelectrolyte complex is by the alternating layer-by-layer deposition method. The preferred concentration of polyelectrolytes in solutions used to deposit in this manner is in the range 0.01 weight % to 10 weight %, and preferably 0.1 weight % to 1 weight %. The polyelectrolyte complex may be prepared by alternately exposing a surface of a substrate to two or more solutions, each comprising a polyelectrolyte until a polyelectrolyte complex of a desired thickness, typically from about 100 nm to about 10,000 nm, is reached. These thicknesses may be typically be achieved by alternately layering between about two and about 1000 nominal layers of polyelectrolyte. At least one solution comprises a predominantly positively charged polyelectrolyte and at least one solution comprises a predominantly negatively charged polyelectrolyte. The alternating polyelectrolyte layering method, however, does not generally result in a layered morphology of the polymers with the film. Rather, the polymeric components interdiffuse and mix on a molecular level upon incorporation into the thin film. See Lösche et al., *Macromolecules* 31, 8893 (1998). The complexed polyelectrolyte within the film has similar morphology as a polyelectrolyte complex formed by mixing solutions of positive and negative polyelectrolyte followed by ultracentrifugation in the presence of salt, as described in the present invention. These polyelectrolyte complex films rarely exceed 1 μm in thickness. While they have sufficient thickness to dampen vibrations between two abutting surfaces separated by a submicron distance, they will typically have insufficient thickness to be used in damping application for macroscopic samples (i.e. of mm or cm dimensions).

For many applications, therefore, thicker polyelectrolyte films may be inserted between two abutting surfaces to dampen vibrations. These thicker films may be prepared in accordance with one method of the present invention. In general, larger quantities of polyelectrolyte complex are typically prepared by combining separate solutions, each containing one of the polyelectrolytes. At least one solution comprises a predominantly positively-charged polyelectrolyte, and at least one solution comprises a predominantly negatively-charged polyelectrolyte. The solutions are combined in a manner that allows the positively-charged polyelectrolyte and the negatively-charged polyelectrolyte to intermix. Intermixing the respective polyelectrolytes causes the in situ formation of a polyelectrolyte complex comprising an intermolecular blend of the positively-charged polyelectrolyte and the negatively-charged polyelectrolyte. Preferably, at least one of the solutions comprises salt ions, such that salt ions also intermix with and become part of the polyelectrolyte complex. The resulting polyelectrolyte complex may simply be allowed to precipitate and settle to the bottom of the container. The supernatant is, in a preferred embodiment, separated to the extent possible from the polyelectrolyte complex. In addition, a substantially compacted article may be obtained by centrifugation at high rates, and particularly in the presence of salt. When a complex is processed thus, it turns from an opaque, gelatinous, diffuse material into a solid plug that it often optically transparent. The plug may be removed and cut into a preferred shape with a razor blade. Accordingly, compacting the polyelectrolyte complex precipitate formed by the intermixing method preferably occurs in a centrifuge capable of obtaining a high rotation rate and g-force to achieve the desired complex modulus, E* or G*. Preferably, the centrifuge is powerful enough to compact the polyelectrolyte complex into a plug, adopting the contours of the centrifuge vessel. Preferably, said vessel is shaped to produce a compacted article of the preferred geometry. More preferably, compaction occurs in the presence of a salt, which appears to enhance the ability of the centrifuge to compact the polyelectrolyte complex. The optimum centrifuging time is a function of the rotor size, defined as the distance between the axis of rotation and the bottom of the centrifuge tube while in motion, the rotation rate, the centrifuging time, the salt concentration, the salt composition, the polyelectrolyte types, the temperature, and the solvent. If pH-dependent groups are present the centrifuge time for compaction also depends on the solution pH. The combination of rotor size and rotation rate is often combined into a single g-force quantity, where the rotational centrifuge force, RCF, in units of g, is given by $RCF=1.12\times10^{-5}\,rN^2$, where r is the radius (cm) of the rotor and N is the rotational speed (rpm).

Centrifugal compaction preferably occurs at speeds of rotation of greater than 10,000 rpm (at a rotor size between about 5 cm and about 30 cm and more preferably at greater than 20,000 rpm (at a rotor size between about 10 cm and about 20 cm). Stated in terms of g-force, centrifugal compaction preferably occurs at g-forces between about 10,000 g and about 1,000,000 g, such as between about 100,000 g and about 500,000 g Centrifuge times between about 1 and about 100 minutes, such as between about 1 and about 10 minutes, at g-forces within the range stated above is typically sufficient to achieve a compacted article comprising polyelectrolyte complex of sufficient density and elastic modulus. As the rotation rate increases the time needed for centrifuging decreases. Increasing the salt concentration decreases the centrifuge time required, sometimes substantially. In some embodiments, the salt concentration is adjusted to be great enough such that the centrifuge time remains below 10 minutes. As a rough guide illustrating the interdependence of required g-forces and salt concentrations for effective polyelectrolyte compaction, the product g[NaCl] should be greater than 10,000. For example, a g-force of at least 10,000 at 1 M NaCl may achieve the desired degree of compaction, whereas a g-force of at least 100,000 may be desired for compaction in the presence of 0.1 M NaCl. More hydrated polyelectrolyte complexes are easier to compact at a given salt concentration. As a rough guide, the formula for minimum g-force may be used: $g[NaCl](100-wt\% H_2O) > 1 \times 10^7$. Where wt % $H_2O$ is the weight percent of water in the compacted complex.

Preferably, centrifugation is performed under conditions of ionic strength greater than 0.1 M. The ionic strength can range quite high, such as between about 0.1 M and about 5 M, preferably between about 0.1 M and about 2.0 M, more preferably between about 0.1 M and about 0.5 M. For example, complexes of PDADMA and PSS have been compacted in 2.5 M NaCl. In one embodiment, centrifugation may occur under conditions in which the sodium chloride concentration is between about 0.1 M and about 0.5 M, preferably between about 0.1 M and about 0.3 M in one embodiment. In another embodiment, centrifugation may occur under conditions in which the calcium chloride concentration is between about 0.1 M and about 0.4 M, preferably between about 0.15 M and about 0.3 M. These ionic strengths may be used to achieve compacted articles having G* at 10 Hz between about 1 kPa to about 300 MPa, more typically between about 10 kPa and about 100 MPa, even more typically between about 1 MPa and about 20 MPa, such as between about 1 MPa and about 10 MPa. Note that conditions employing higher ionic strength tend to yield a compacted article having G* near the higher end of the range of G* available for a particular polyelectrolyte complex article at a particular salt concentration. For example, centrifugation under conditions of 0.15 M sodium chloride concentration may yield a compacted article having an elastic modulus between about 1 and about 5 MPa. Preferably, the centrifugal compaction is performed at ionic strength higher than that at which the article is to be used. Preferably the ionic strength at which centrifugal compaction takes place is at least 20% greater than the ionic strength at which the article is used. The reason for the elevated ionic strength during centrifugation is that it facilitates the compaction process. For example, a polyelectrolyte complex may be compacted at 2.0 M salt concentration and then employed for use, for example as an in-vivo implanted medical device, at about 0.15 M electrolyte concentration (i.e. physiological). Excess salt, generated by the release of ions from the polyelectrolytes during precipitation, may be removed by washing or by dialysis.

A variety of salts, comprising monovalent or polyvalent cations and/or monovalent or polyvalent anions, may be used during the centrifugal compaction process. Preferably, the salt is NaCl. The salt may be present at the polyelectrolyte precipitation stage, or it may be present at the centrifugation stage. Preferably, a lower concentration of salt is present during precipitation, for example in the range of 0.1M, and a higher concentration is present during centrifugation, in the range of 1.0 M.

For applications requiring the insertion of compacted article comprising polyelectrolyte complex in vivo, as a medical implant, it is not advantageous to use salt concentrations significantly higher than 0.15 M. This is because the osmotic pressure can shock surrounding tissue. However, it is advantageous to introduce the compacted object having a more flowable character and allow it to harden in vivo. For this purpose, it is preferable to employ a salt of calcium, aluminum or magnesium, preferably the chloride or citrate salt, in the centrifugal compaction process at physiological osmotic pressure, introduce the implant, then allow the implant ions to be replaced by physiological ions (i.e. mostly NaCl). Compacted complexes comprising substantially salts of calcium, aluminum or magnesium are more flowable than compacted complexes comprising NaCl at the same ionic strength.

If large changes in ionic strength between compaction and use are to be avoided, it is preferable to use a salt of calcium, aluminum, or magnesium preferably the citrate, chloride, or bromide during the compaction step. The use of salts other than sodium chloride is preferred when the ionic strength of NaCl required for good compaction is greater than about 2 M. As the concentration of salt increases the density of the solution increases. The higher solution density leads to less efficient centrifugal compaction. Therefore, the use of another salt, having improved compaction properties at lower concentration, is preferred. Examples of said alternative salts include those from calcium, aluminum or magnesium.

Optionally, heat may be applied to the solution during centrifugation. The purpose of the heat is to render the materials in the centrifugation process more flowable (lower viscosity). Preferably, the solution is heated between 30 and 90 degrees centigrade. Higher temperatures are possible, but the centrifuge container must be pressurized, as the solutions will boil at about 100 degrees centigrade.

Alternatively, the polyelectrolyte complexes may be compacted under pressure. In this method, individual polyelectrolytes in solution are mixed, preferably in the presence of salt. The gelatinous precipitate is then pressed against a filter membrane by hydrostatic pressure. The hydrostatic pressure may be between about 40 psi and about 10,000 psi, such as between about 100 psi and about 1000 psi, to achieve a compacted polyelectrolyte complex article of desired modulus and density. The gelatinous polyelectrolyte complex suspension tends to plug up the pores of the filtration media, therefore, the filter medium preferably has pores of diameter less than 10 micrometer in diameter, more preferably of molecular dimensions of the solution polyelectrolytes. Pores of such small dimensions are obtained from porous anodized alumina or track-etched polymer membranes (e.g. "Nucleopore" which is track-etched polycarbonate). Examples of filters with pores smaller than polymer molecule dimensions include dialysis tubing (e.g. treated cellulose films) and membranes that are used in the art for reverse osmosis. The advantage of membranes with pores smaller than the molecular dimensions is that the polymer molecules do not plug the pores, while the disadvantage is that the filtration is slow. For precipitates that clog filters excessively, it is advantageous to employ filter media that have graded pore sizes, from larger to smaller pores going into the medium.

In yet another alternative, the polyelectrolyte complexes may be compacted under vacuum. In this method, individual polyelectrolytes in solution are mixed, preferably in the presence of salt. The gelatinous precipitate is then pressed against a filter membrane. A vacuum is then applied on the opposite side of the membrane, the vacuum being sufficient to pull water from the precipitate by suction. The gelatinous polyelectrolyte complex suspension may tend to plug up the pores of the filtration media, therefore, the filter medium preferably has pores of diameter less than 10 micrometer in diameter, more preferably of molecular dimensions of the solution polyelectrolytes.

Preparation of the compacted article comprising polyelectrolyte complexes according to the method of the present invention provides many advantages.

First of all, the method enables the preparation of articles having a wide range of transverse dimensions, such as, on the order of micrometers, millimeters, and even centimeters, wherein the transverse dimension is the distance between one surface of the article to another, opposing surface of the article. The transverse dimensions of the compacted articles may be a function of the desired gap distance between two abutting surfaces and the shape of the gap between the abutting surfaces, wherein the compacted article is placed in the gap between two abutting surfaces to dampen vibrations. In general, compacted articles comprising polyelectrolyte complexes may be prepared in which the article's transverse dimensions are no less than about 10,000 nm, no less than about 100 micrometers, no less than about 1 mm, or more, such as no less than about 1 cm, no less than about 2 cm, no less than about 5 cm, or even no less than about 10 cm. For example, a compacted article may be prepared in the shape of a cube or rectangle, in which the transverse dimensions comprise a length, a width, and a thickness, whereby each of these transverse dimensions is no less than about 10 micrometers, no less than about 100 micrometers, no less than about 1 mm, or more, such as no less than about 1 cm, no less than about 2 cm, no less than about 5 cm, or even no less than about 10 cm. Other shapes are possible. For example, the compacted article may be prepared as a sphere, in which the transverse dimension comprises a diameter, whereby the diameter is no less than about 10 micrometers, no less than about 100 micrometers, no less than about 1 mm, no less than about 1 cm, no less than about 2 cm, no less than about 5 cm, or no less than about 10 cm. In yet another alternative, the compacted article may be prepared as a spheroid, either prolate or oblate, in which the transverse dimensions comprise major and minor axes, whereby each of the major and minor axes are no less than about 10 micrometers, no less than about 100 micrometers, no less than about 1 mm, no less than about 1 cm, no less than about 2 cm, no less than about 5 cm, or even no less than about 10 cm.

Compacted articles having these transverse dimensions are particularly suitable for damping applications, whereby the compacted article may be inserted in a gap between two abutting surfaces. The compacted article, for example, may be prepared to have a complex shear modulus between about 1 kPa and about 300 MPa at a frequency between about 0.1 Hz and about 10,000 Hz, such as between about 1 kPa to about 300 MPa at a frequency of about 10 Hz. Moreover, the compacted article may be prepared to have a loss factor of at least about 0.2 at a frequency between about 0.1 Hz and about 10,000 Hz, such as at least about 0.2 at a frequency of about 10 Hz. Accordingly, the compacted articles may be used in materials requiring damping vibrations over a wide range of gap sizes and over a wide range of vibration frequencies.

Moreover, the preparation of the complex by either of the multilayering or precipitation methods followed by compaction in solution yields a homogenous product. The method of the present invention advantageously avoids the precipitation of salt crystals since the salt ions associated with the charged repeat units on the positively and negatively charged polyelectrolytes, rather than precipitated with the bulk of the compacted articles. Accordingly, the bulk of the compacted article comprising polyelectrolyte complex is substantially free of crystals comprising salt ions having a size greater than about 1 micron. Advantageously, the complex is substantially free of crystals having a size greater than about 100 nm. Crystal size and number density within the bulk of the compacted article may be determined empirically by microtoming, in which sections of the compacted article may be analyzed by an electrical microtome, for example the Micron HM200 Ergostar (available from MICROM International GmbH).

Further, the preparation method of the present invention yields a compacted article having a minimum number of pores or voids (remaining after previously formed salt crystals have been dissolved), such that the material is dense. For example, a compacted article comprising polyelectrolyte complex may be prepared that is substantially free of voids having a size greater than about 1 micron when the bulk of the polyelectrolyte complex is characterized by a doping level ratio between about 0.01 and about 0.50 (i.e., has a doping level percentage between about 1% to 50%), such as between about 0.02 and about 0.20 (i.e., between about 2% and about 20%). Advantageously, the complex is substantially free of voids having a size greater than about 100 nm at these doping levels.

The method of the present invention enables the incorporation of a wide variety of additives into the bulk of the compacted article comprising polyelectrolyte complexes. For example, articles that are to be implanted in vivo may optionally further comprise antibacterial and/or anti-inflammation and/or antirejection agents. These additives respectively aid in reducing infection, inflammation or rejection of the implanted article. Examples of antibiotics are well known to the art and are to be found in E. M. Scholar, The antimicrobial drugs, New York, Oxford University Press, 2000 or the Gilbert et al., The Stanford Guide to Antimicrobial Therapy, Hyde Park, Vt., 2000, or the R. Reese, Handbook of Antibiotics, Philadelphia, Lippincot, 2000. Antibacterial agents include silver. These additives may be incorporated prior to precipitation, prior to centrifugation, or after centrifugation. Preferably, the additives are mixed with the polyelectrolytes before the precipitation stage. The advantage of introducing additives prior to precipitation is that the additives are incorporated throughout the polyelectrolyte complex. On the other hand, if minimizing the waste of additive is a concern, the additives are added during centrifugation, after much of the supernatant liquid is poured off.

Additionally, compacted articles comprising polyelectrolyte complex exhibit good shape memory. If an article is to be used for mechanical damping, it is desirable that any mechanical deformation of the article induced by transient stress be completely reversible. That is, when the stress is removed from the article it recovers its original dimensions. If the original dimensions are recovered instantly the article is said to be elastic. If the original dimensions are recovered over time, the article exhibits viscoelastic response. If the article does not recover its original dimensions, it is irreversibly deformed. As a test of the recovery properties of the compacted article of present invention, a piece of it was severely deformed (see Example below). It was observed to recover its original dimensions after some delay. Such deformation/recovery cycling is sometimes termed "shape memory." The mechanical behavior of an intervertebral disk is viscoelastic. Therefore, the present invention advantageously reproduces the mechanical properties of a disk.

Preferred Applications

A preferred application of compacted article comprising polyelectrolyte complex is a viscoelastic fluid filler in a mechanical damping piston. Said piston preferably comprises a piston and a sleeve, wherein the piston traverses the sleeve. Such an arrangement is typical in shock absorbers installed on vehicles. Preferably, there is an orifice in the piston or the sleeve which constrains the movement of the hydraulic fluid, which is, in the present case, the compacted article. The size of the orifice is adjusted to allow the desired flow rate of hydraulic fluid. The hydraulic fluid is preferably sealed within the shock absorber. The damping amplitude and optimal damping frequency is preferably selected by selecting the appropriate combination of polyelectrolytes and salt concentration. Several advantages of using a compacted polyelectrolyte complex article over conventional hydrocarbon-based oils are apparent: 1) since the hydraulic fluid is based on aqueous complexes rather than hydrocarbon oils the system is less harmful to the environment and 2) The viscoelastic properties of a particular compacted article can be tuned over a wide range by the addition of salt, whereas in oil-based hydraulics the oil must be removed and replaced to change the viscoelastic response.

In another application, the compacted article comprising polyelectrolyte complex is used as a shock absorbing pad. The vibrations at a tabletop or work surface may be diminished by placing compacted article comprising polyelectrolyte complex between the surface and the noisy environment. The article is preferably cut to the desired size and shape and sealed, preferably within a bag or pouch made of impervious polymer, preferably a polyolefin. Sealing is preferred, as the water content within the compacted article is essential to maintaining the desired viscoelastic properties. Preferably, the compacted article comprising polyelectrolyte complex exhibits minimal irreversible flow over the long term. The complex shear modulus of compacted article comprising polyelectrolyte complex is at least 1 kPa and preferably at least 100 kPa over the frequency range 01. to 10,000 Hz. Preferably tan($\Delta$) is greater than 0.25. In certain environments, such as the marine environment, sealing may not be required. For example, if a joint is to be caulked with a compacted article with the objective of reducing vibrations in a marine environment, sealing is not required as long as said joint remains in contact with water.

Another preferred application of the compacted article comprising polyelectrolyte complex is as a replacement for soft skeletal material, particularly the disks between spinal vertebrae.

One example of an artificial intervertabral disk is the Charite™ artificial disk by DePuy Spine Inc., approved by the FDA in 2004. This disk comprises polyethylene sandwiched between metal plates. While the Charite disk allows natural spine flexion, the modulus of the materials used is much higher than that of a natural intervertebral disk such that the artificial disk does not have the same damping (shock absorption) properties.

One approach to replacing disks is to fill intervertebral cavities with a natural polyelectrolyte complex comprising cells that will form new tissue. Cells have been immobilized in polyelectrolyte gels. For example, Lim and Sun (Science, 210:908-910 (1980)) described Islets of Langerhans immobilized in natural polyelectrolytes (alginate gels). There are several potential problems with this. First, natural polyelectrolyte gels tend to be very low modulus and cells take time to grow into fully functional tissue. Thus, the patient will not be able to place full mechanical load on the growing disk before it has fully formed. Second, natural polyelectrolytes, such as chitosan and hyaluronic acid are substrates for cell metabolism. They may be metabolized too quickly and by other cells. Third, nerve cells can grow into disks, which create pain. For these and other reasons, the compacted article of the present invention preferably comprises at least one polyelectrolyte comprising synthetic or non-natural repeat units. The synthetic repeat units are less likely to be degraded/consumed in vivo. Preferably all the polyelectrolytes comprise synthetic repeat units.

As can be seen from the examples below, compacted polyelectrolyte complexes have favorable complex shear modulii. For example the poly(styrene solfonate)/poly(diallyldimethylammonium) (PSS/PDADMA) complex has a G* of about 15 MPa in 0.15M NaCl. This compares favorably with the modulus of a complete intervertebral disk of 1 MPa to 25 MPa.

An intervertebral disk comprises the nucleus pulposus (an interior gel), and the annulus fibrosus (which is tougher and fibrous). Commonly, the annulus tears and the nucleus leaks out. The disk loses thickness and damping capability and may impact the spinal cord or cause irritation. Optionally, the nucleus pulposus is replaced by a compacted polyelectrolyte complex article. The polyelectrolyte complex is soft but will not leak out. The additional material added to the disk will separate the vertebrae, reducing deformities of the spine.

Optionally, the compacted article comprising polyelectrolyte complex is injected into the intervertebral space by means of a needle or cannula. In this procedure, the vertebrae are mechanically stabilized with clamps. Polyelectrolyte complex disk material is injected between vertebrae. Excess salt is then washed away with excess saline solution. The disks are allowed to harden and then the clamps are removed after all the excess salt is washed away.

In some applications, such as the replacement of an intervertebral disk, the compacted article preferably comprises higher modulus material on the outside or periphery or surface stratum of the article and a lower modulus in the interior region of the article. The lower modulus in the interior or interior region serves to absorb more shock, and the higher modulus in the periphery or surface region serves to retain the shape and integrity of the compacted article comprising polyelectrolyte complex. Accordingly, in one aspect of this invention, there is a gradient in modulus within the compacted article. Such a gradient is preferably achieved by crosslinking polyelectrolyte located in the surface region of the article. Crosslinking is accomplished by heat treatment, by infusing crosslinking agents into the article from the outside in, or by photocrosslinking the article. The advantage of photocrosslinking the compacted article is that the penetration depth of the light into the compacted article may be controlled by the wavelength selected, such that the crosslinking occurs only within thin surface region on the external surface of the compacted article. Preferably the modulus of the surface region of the compacted article comprising polyelectrolyte complex is at least 2 times greater, preferably at least about 5 times greater, even more preferably at least about 10 times greater than the modulus of the bulk region of the compacted article.

Biocompatibility

It has been shown that certain polyelectrolytes or polymers are biocompatible. For example, a biocompatible polyelectrolyte multilayer, on which smooth muscle cells were grown, has been described by Schlenoff et al (U.S. Pub. No. 2005/0287111) which is herein incorporated by reference. This multilayer comprised fluorinated polyelectrolyte complex, on which cells grow. However, the cells do not consume the fluorinated material. In one aspect of the present invention, therefore, the compacted polyelectrolyte complex article further comprises a surface stratum of fluorinated polyelectrolyte. The surface stratum is preferably obtained by immersing the compacted polyelectrolyte complex article in a solution of fluorinated polyelectrolyte. The process may be repeated with alternating positive and negative fluorinated polyelectrolytes to obtain a thicker surface stratum. In one embodiment, the alternating layering to buildup the surface stratum comprising fluorinated polyelectrolyte may be repeated to deposit between about one and about 1000 positively and negatively charged fluorinated polyelectrolyte pairs, preferably between about one and about 250 positively and negatively charged fluorinated polyelectrolyte pairs.

Bioinertness

It has been shown that a polyelectrolyte complex film comprising a zwitterion repeat unit has bioinert properties, i.e., the adsorption of proteins, cells and other biological materials is minimized on the film. Examples are provided in U.S. Pub. No. 2005/0287111). Therefore, in one aspect of the present invention, the compacted polyelectrolyte complex article further comprises a surface stratum comprising polyelectrolytes comprising zwitterionic repeat units. Other bioinert materials are known to the art, such as poly(ethylene glycols), PEG. Therefore, in one aspect of this invention, the compacted polyelectrolyte complex article further comprises a surface stratum of PEG.

Other biological materials are known to be biocompatible, such as serum albumin. In one embodiment, the compacted polyelectrolyte complex article may be coated with serum albumin on exposure to in vivo conditions (i.e. following implant).

Having described the invention in detail, it will be apparent that modifications and variations are possible without departing from the scope of the invention defined in the appended claims.

EXAMPLES

The following non-limiting examples are provided to further illustrate the present invention.

In the examples, the following shorthand for polyelectrolyte complexes built on substrates is employed: $(A/B)_x$ where A is the starting polyelectrolyte contacting the substrate, B is the terminating polyelectrolyte in contact with subsequent protein solutions and x is the number of layer pairs. In $(A/B)_x$ A, A would be the terminating polymer. Salt, MY (cation M and anion Y), has an important role in the buildup process and is represented by $(A/B)_x$ @ c MY, where c is the molarity of the salt (MY) in the polymer solution. The pH can be included in the nomenclature esp. when using pH dependent polyelectrolytes. For example, $(PAH/PAA)_2PAH$ @ 0.25 M NaCl @ pH 7.4, represent two layers pairs of PAH/PAA built at 0.25 M NaCl and a pH of 7.4.

Example 1

Static Stress-Strain Behavior of Polyelectrolyte Complex

Several compacted polyelectrolyte complexes were prepared by the multilayer method on a Teflon substrate. Free polyelectrolyte complexes were exposed to salt solutions of various concentrations for durations sufficient to equilibrate the bulk salt concentration of the polyelectrolyte complex with the salt solution. After equilibration, the elastic moduli of the polyelectrolyte complexes were measured.

Poly(styrene sulfonic acid) (PSS, molecular weight $6.8 \times 10^4$, $M_w/M_n=1.06$) and poly(diallyldimethylammonium chloride) (PDADMA, molecular weight $3.7 \times 10^5$, $M_w/M_n=2.09$) were obtained from Aldrich. Sodium chloride (NaCl) was obtained from Fisher. Deionized water (Barnstead, E-pure, Milli-Q) was used to prepare all aqueous solutions.

Two polyelectrolyte solutions were prepared, one comprising PSS and one comprising PDADMA. The polyelectrolyte concentration was 0.01 M (with respect to the monomer repeat unit) and the sodium chloride concentration was 1.0 M.

The poly(tetrafluoroethylene) (Teflon™) substrate (50 mm length×24 mm width×1.6 mm thickness) was cleaned in ethanol. The PDADMA/PSS polyelectrolyte complex was built upon the substrate according to the multilayer method by alternately exposing the substrate to the two polymer solutions for 5 minutes using a robotic platform (StratoSequence, nanoStrata Inc.) with three rinses of deionized water for 1 minute each. Rinse and polymer solution volumes were 50 mL. The polyelectrolyte complex was annealed at room temperature in a sodium chloride solution (1.0 M) for one week.

The "dry" thickness of the multilayer was determined using Fourier Transform Infrared Spectroscopy (FTIR) comparison (using the strong sulfonate stretch at 1100 cm$^{-1}$) of a PDADMA/PSS polyelectrolyte complex of known thickness (measured with a Gaertner Scientific L116S ellipsometer) with the "thick" PEMU used for mechanical analysis.

The PDADMA/PSS polyelectrolyte complex was pealed off the Teflon™ substrate using flat-ended tweezers and cut into microcoupons (2.0 mm length×150 μm width×9.0 μm dry thickness) with a razor blade. Both ends of a microcoupon were wrapped around aluminum foil clips and secured thereto by applying a drop of silicone rubber before closing the clips.

The aluminum clips were connected to minuten pin hooks on a capacitance-type force transducer (3.3 kHz resonant frequency; Aurora Scientific, Ontario, Canada, calibrated with small weights), and a moving iron galvanometer motor (step time≦300 μs; Aurora Scientific, Ontario, Canada), designed for monitoring contractile behavior of single muscle fibers, mounted on the base of a Leitz Diavert (Wetzlar, Germany) inverted microscope. Silicone sealant was used to stabilize the clips on the minuten pins. Position was monitored by a capacitance-type transducer in the motor. Calibration was done by applying a control voltage input (square wave) to the motor, and measuring (using a microscope) the linear distance traveled in the horizontal plane by a clip attached to the motor hook. This allowed for rapid determination of the delta-position for a given input wave amplitude.

A temperature controlled stage containing six salt solutions of variable ionic strength (0.0 M, 0.2 M, 0.4 M, 0.6 M, 0.8 M. and 1.0 M sodium chloride) was used to soak the polyelectrolyte complex microcoupons for in situ measurements. The salt solutions were held in 200-μL anodized aluminum wells. The temperature was maintained at 28±1° C. with an ATR-4 regulator (Quest Scientific, North Vancouver, BC, Canada). Before every measurement, the polyelectrolyte complex microcoupon was conditioned in the salt solution for 10 minutes. Experimental control, data collection, and analysis of raw data were carried out using a PC-based system with a DT2831-G board (Data Translation, Marlboro, Mass.) and custom software. The software performs a fast Fourier transform method, converts to polar notation, finds the maximum amplitude index, calculates stiffness values and phase shift values, writes them to a file, converts to complex notation, and performs an inverse fast Fourier transform. Force was normalized to the polyelectrolyte complex microcoupon cross-sectional area, which was calculated from the wet thickness at different salt concentrations.

FIG. 1 shows the stress-strain behavior of the (PDADMA/PSS)$_{250}$@1.0M NaCl polyelectrolyte complex at different salt concentrations. The curves correspond to salt concentrations as follows: (open circle) 0.0 M NaCl solution; (asterisk) 0.2 M NaCl solution; (triangles) 0.4 M NaCl solution; (crosses) 0.6 M NaCl solution; (squares) 0.8 M NaCl solution; (diamonds) 1.0 M NaCl solution correspond to the stretching cycle (in increasing order of elongation) while (solid circles) 0.0 M NaCl solution; (solid triangles) 0.4 M NaCl solution; and (solid squares) 0.8 M NaCl solution indicate a decreasing elongation cycle.

Figure 2:
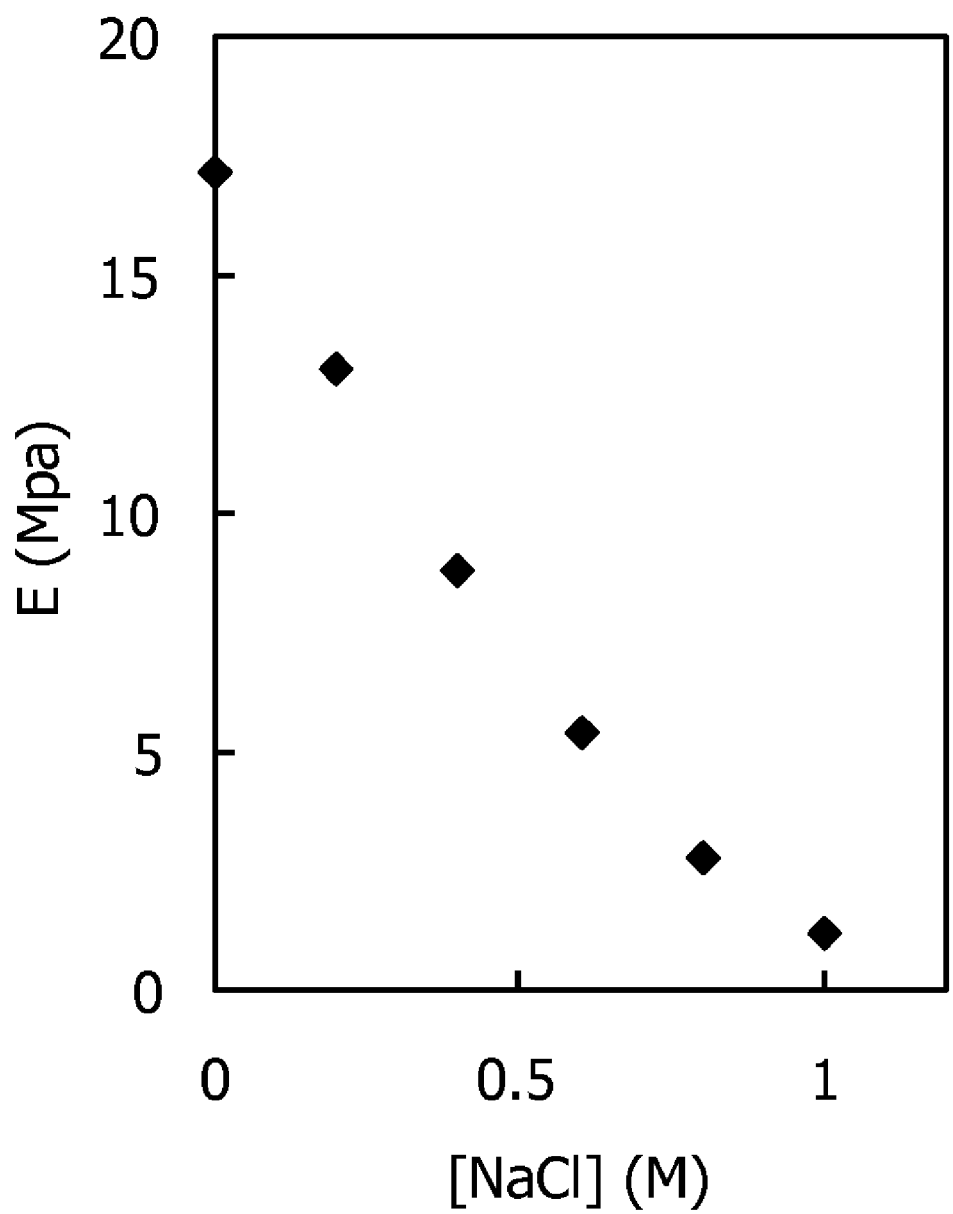
FIG. 2 is a graph showing the Elastic Modulus of a polyelectrolyte complex after conditioning at several ionic strengths. The data in the graph were obtained according to the method of Example 1.

FIG. 2 shows the elastic modulus, E, of the (PDADMA/PSS)$_{250}$@1.0M NaCl polyelectrolyte complex at different salt concentrations. The elastic modulus is obtained from the slope of the curves in FIG. 1. At 0.0 M NaCl, E=17 MPa. Elastic modulus, E, measures the resistance to deformation of a material when stress is applied. Elastic modulus is defined according to the following equations:

$$E = \frac{\sigma}{e}$$

$$e = \frac{L - L_0}{L_0}$$

wherein e is the strain, σ is the stress, and L$_0$ and L are the length of the polyelectrolyte complex at rest and the length of the polyelectrolyte complex after applying a certain strain, respectively.

In agreement with these Equations the relationship between applied strain and resulting stress in polyelectrolyte complex for e<2% (i.e, percent of elongation less than 2% of length of polyelectrolyte complex at rest) was found to be linear. Further, when the elongation cycle was repeated at a certain ionic strength, σ$_{eq}$ was reproducible with minimal hysteresis. This means that the multilayer recovered almost completely when the applied strain is removed (i.e. there was no residual deformation).

Elastic modulus, E, evaluated from the slopes of the stress-strain data as show in FIG. 2, was observed to decrease as the ionic strength increased. That is, the polyelectrolyte complex material becomes softer as more salt is added.

Example 2

Dynamic Storage Modulus of Polyelectrolyte Complexes

The damping behavior of polyelectrolyte complex was tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 1% of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, σ, was recorded.

Figure 3:
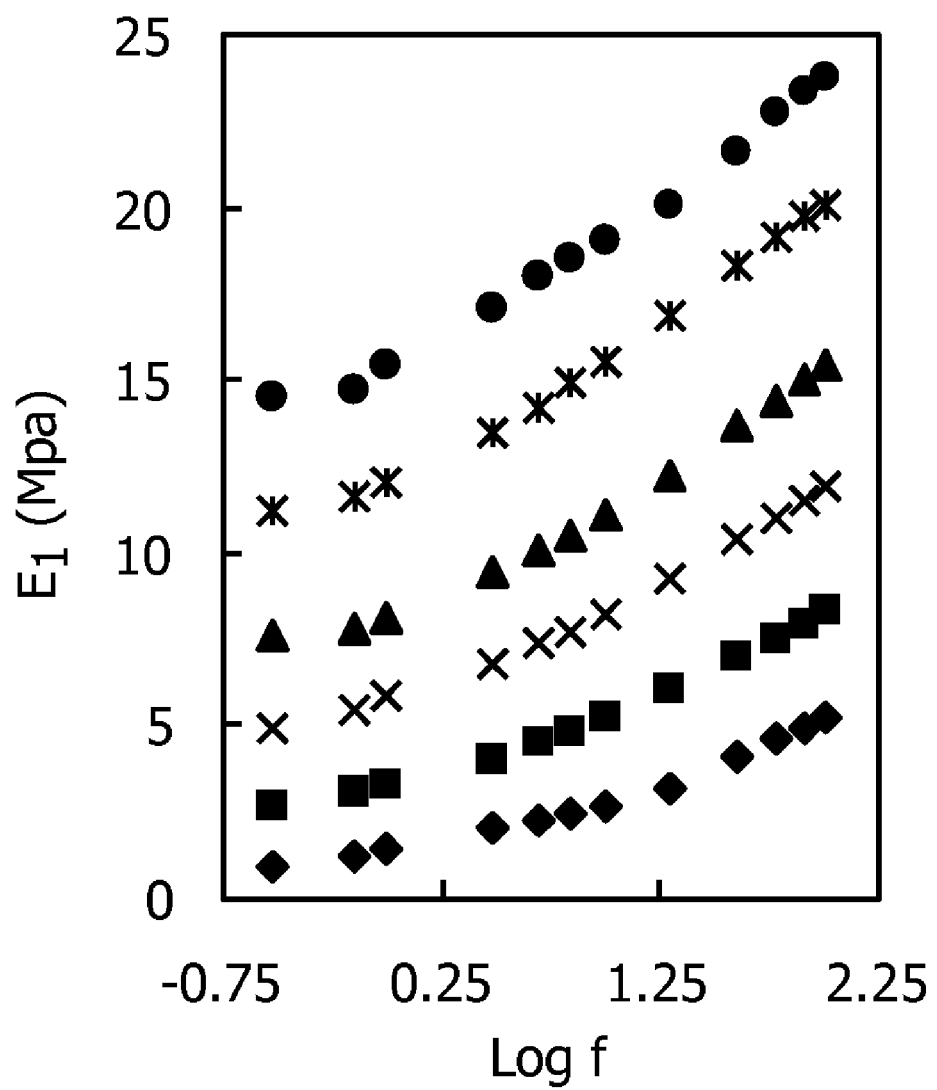
FIG. 3 is a graph showing the Dynamic Storage Modulus behavior of a polyelectrolyte complex after conditioning at several ionic strengths. The data in the graph were obtained according to the method of Example 2.

When a polyelectrolyte complex microcoupon was oscillated sinusoidally (frequency, f=0.1-100 Hz), at constant ionic strength, the relationship between E$_1$ and f showed two distinct regions. See FIG. 3, which shows the dynamic storage modulus behavior of the (PDADMA/PSS)$_{250}$@1.0M NaCl polyelectrolyte complex at different salt concentrations as a function of frequency (Hz). The curves correspond to salt concentrations as follows: (solid circles) 0.0 M NaCl solution; (asterisks) 0.2 M NaCl solution; (solid triangles) 0.4 M NaCl solution; (crosses) 0.6 M NaCl solution; (solid squares) 0.8 M NaCl solution; (solid diamonds) 1.0 M NaCl solution. The stress was corrected for actual cross-sectional area of the microcoupons, with consideration of water volume fraction.

At low frequency (0.1-1.0 Hz), the polyelectrolyte complex had enough time to reorient to a new lower free energy state before the next deformation cycle, such that the complex exhibits rubber-like behavior. At high frequency (f>1.0 Hz) or at short time, the polymer chains do not have enough time to relax, such that the complex exhibits glassy behavior.

Example 3

Dynamic Loss Modulus of Polyelectrolyte Complexes

The energy dissipation behavior of polyelectrolyte complex was tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 1% of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, σ, was recorded.

Figure 4:
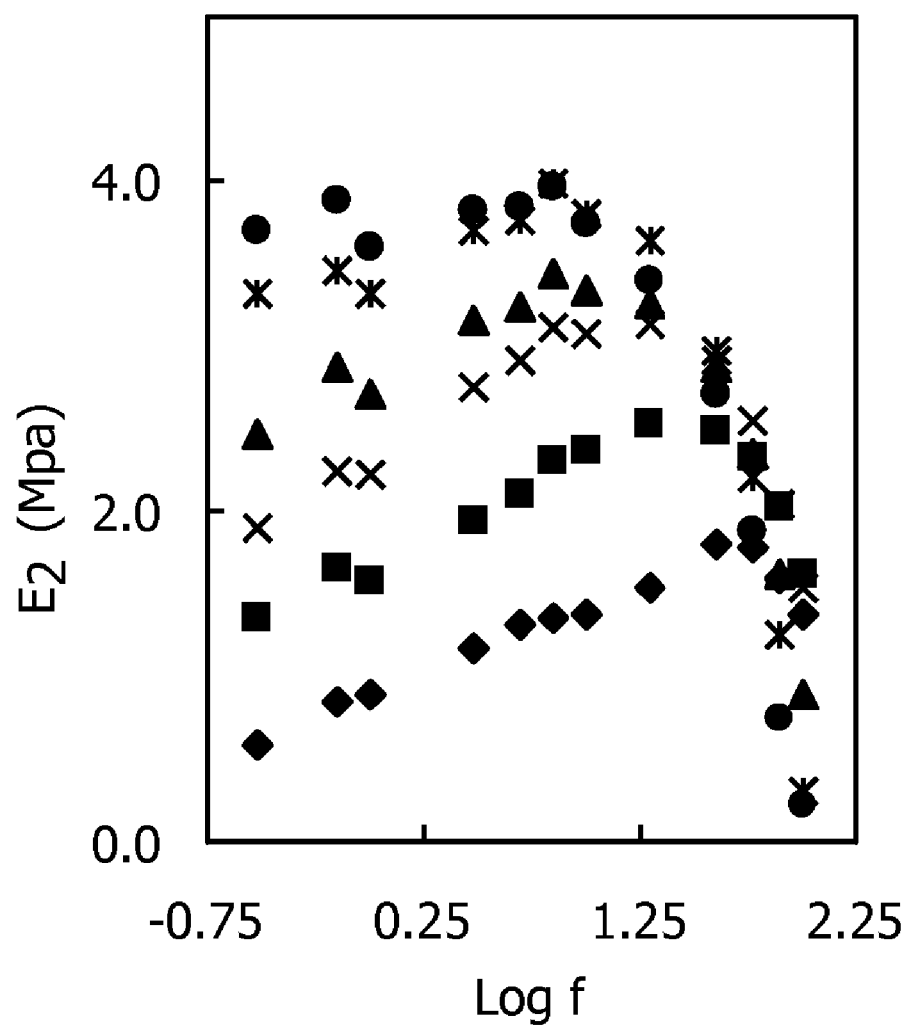
FIG. 4 is a graph showing the Dynamic Loss Modulus behavior of a polyelectrolyte complex after conditioning at several ionic strengths. The data in the graph were obtained according to the method of Example 3.

FIG. 4 depicts the isothermal loss modulus spectra of the polyelectrolyte complex immersed in the salt solutions of various ionic strengths. The curves correspond to salt concentrations as follows: (solid circles) 0.0 M NaCl solution; (asterisks) 0.2 M NaCl solution; (solid triangles) 0.4 M NaCl solution; (crosses) 0.6 M NaCl solution; (solid squares) 0.8 M NaCl solution; (solid diamonds) 1.0 M NaCl solution. The stress was corrected for actual cross-sectional area of the microcoupons, with consideration of water volume fraction. According to FIG. 4, E$_2$, was also found to be a function of the rate of the applied strain and the salt concentration of the bathing medium.

In contrast to the low frequency region, where E$_2$ increased with frequency, irrespective of solution ionic strength, the loss modulus deteriorated toward the high frequency end of the spectrum. However, as the salt concentration decreased below 1.0 M, the loss modulus peak broadened progressively. Since E$_2$ is directly proportional to E$_1$ (E$_2$=E$_1$ Tan Δ), the whole curve shifted towards a lower value of E$_2$ when the ionic strength of the medium increased.

When different systems are compared at the same strain amplitude, E$_2$ serves as a measure of the energy dissipated per cycle. Typically, viscoelastic polymers show E$_2$ values in the range of 0.03-0.05 MPa at 1-10 Hz. At the same frequency range, the polyelectrolyte complex has a loss modulus of 0.5-1.5 MPa and 3.5-4.0 MPa at 1.0 and 0.0 M NaCl respectively. Therefore polyelectrolyte complexes exhibit significant increases in energy dissipation compared to conventional viscoelastic materials.

Example 4

Loss Factor of Polyelectrolyte Complexes

The damping properties of polyelectrolyte complex were tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 1% of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, σ, was recorded.

In dynamic modulus analysis, the strain will be out of phase with the stress (i.e., viscoelastic lag) due to the time necessary for molecular rearrangements. Accordingly, it is possible to probe the extent of damping in polyelectrolyte complexes via the phase angle, Δ.

Figure 5:
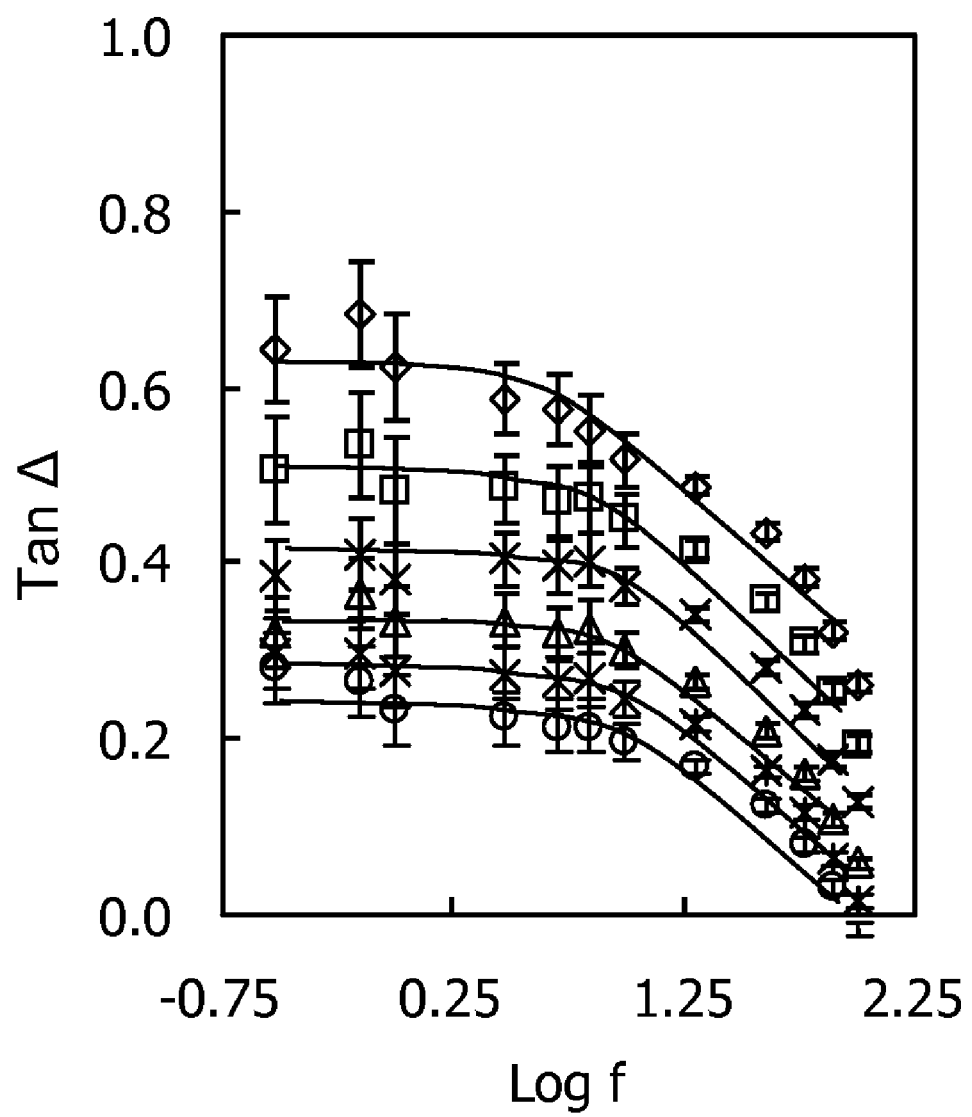
FIG. 5 is a graph showing the damping behavior of a polyelectrolyte complex after conditioning at several ionic strengths. The data in the graph were obtained according to the method of Example 4.

FIG. 5 depicts the damping behavior of polyelectrolyte complex immersed in the salt solutions of various ionic strengths. The curves correspond to salt concentrations as follows: (open circles) 0.0 M NaCl solution; (asterisks) 0.2 M NaCl solution; (open triangles) 0.4 M NaCl solution; (crosses) 0.6 M NaCl solution; (open squares) 0.8 M NaCl solution; (open diamonds) 1.0 M NaCl solution. Solid lines are guides to the eye.

FIG. 5 shows quantitatively that the polyelectrolyte complex was able to dissipate a larger fraction of energy at higher ionic strength. The effect of ionic strength and applied frequency on the damping ability of the multilayer can be summarized as follows: In the low frequency region (0.3-10 Hz), Tan(Δ) remained fairly constant, especially at salt concentrations above 0.2 M. It started to decline at about 20 Hz and progressively deteriorated as the multilayer response became more glassy-like (f>20 Hz). As the salt concentration decreased, damping was observed to diminish.

Compared to other commercially available polymer damping materials such as acrylic adhesives39 (127 μm thick; Tan Δ of 0.38) and rubber adhesives39 (280 μm thick; Tan Δ of 0.25) see Biggerstaff, J. M.; Kosmatka, J. B. J. Compos. Mater. 1999, 33, 1457, Polyelectrolyte complex ((PDADMA/PSS)$_{250}$@1.0M NaCl) at 9.0 μm dry thickness (Tan Δ of 0.62) showed up to 250% enhancement in damping properties over the range of 0.3-10 Hz. Moreover, the polyelectrolyte complex was much thinner than conventional damping adhesives. Damping on such a small length scale might have utility in MEMS systems.

Example 5

Centrifugal Compaction of Polyelectrolyte Complex Using and Ultracentrifuge A compacted article comprising polyelectrolyte complex was prepared. Two solutions were prepared, each comprising polyelectrolyte. One solution was prepared by dissolving poly(diallyldimethylammonium chloride) (PDADMAC, 10 wt. %) and sodium chloride (2.5 M) in water. One solution was prepared by dissolved poly(stryrene sulfonate) (PSS, 10 wt. %) and sodium chloride (2.5 M) in water. The solutions were mixed in a beaker and stirred with the aid of a magnetic stir bar. A gelatinous precipitate formed.

The precipitate was allowed to settle and most of the supernatant was poured off. The precipitate was placed in a centrifuge tube, and the tube place in a type TL series 90 Ti rotor. The rotor was placed in a Beckman ultracentrifuge, and the precipitate was centrifuged at 25° C. at 55,000 rpm for 4 hours. An optically transparent solid compact plug of polyelectrolyte complex formed at the bottom of the tube, and the excess liquid was poured off. The plug was removed and cut with a razor blade into shapes for mechanical testing.

Example 6

Modulus of Centrifugally Compacted Polyelectrolyte Complex

Figure 6:
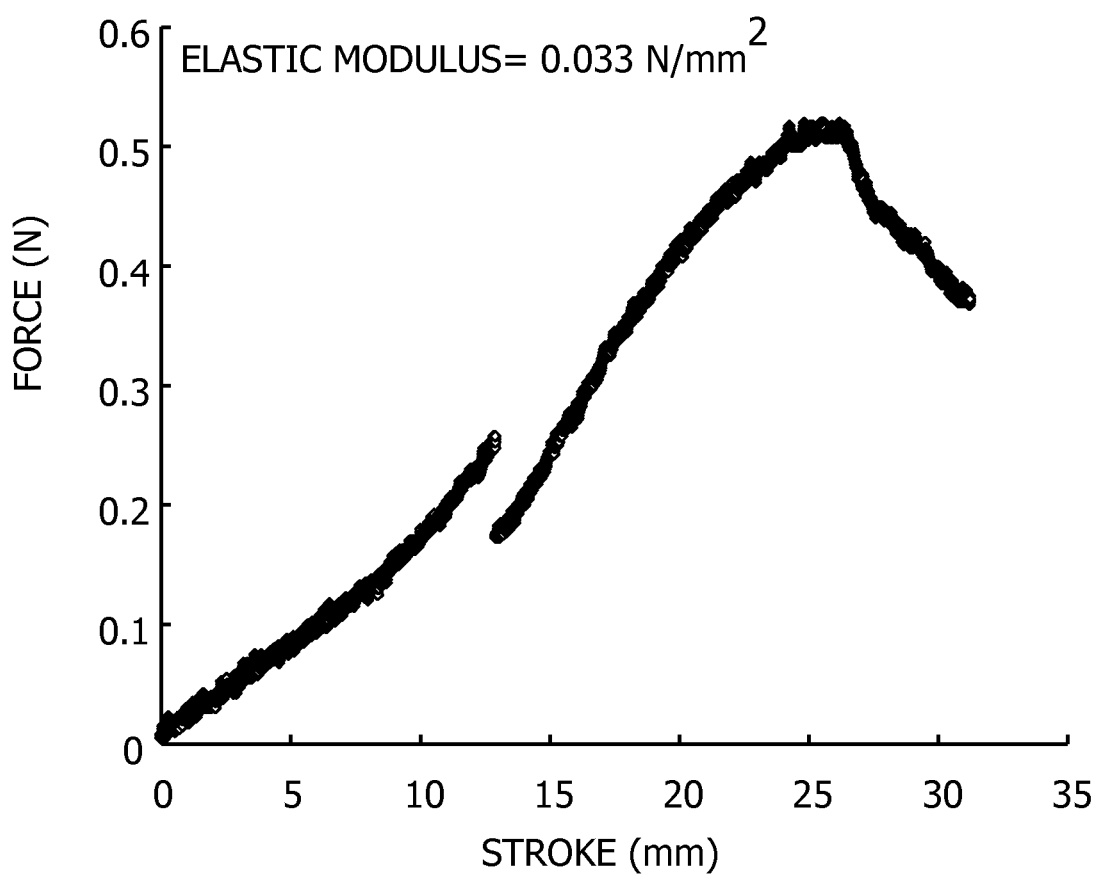
FIG. 6 is a graph showing the Elastic Modulus of a compacted article comprising polyelectrolyte complex formed into a rectangular sheet having millimeter dimensions. The data in the graph were obtained according to the method of Example 6.

The static elastic modulus of the glassy compacted plug comprising PSS/PDADMA prepared according to the method of Example 5 was tested. A sample was cut into flat rectangular sheets of dimension 3 mm×7 mm×26 mm. Each sheet was placed into an Instron mechanical stretching apparatus. The apparatus records the force (Newtons) and the stroke (mm) as the sample is stretched. The sample was not allowed to dry. FIG. 6 depicts a force vs. stroke graph for one sample. The elastic modulus for this particular sample was 0.033 N/mm$^2$ (0.033 MPa). The elastic modulus of five samples was measured and the average modulus was 0.3 N/mm$^2$ (0.3 MPa).

Example 7

Shape Memory

The ability of the glassy compacted plug comprising PSS/PDADMA plug prepared according to the method of Example 5 to remember its shape after deformation was tested. The compacted plug was cut into a rectangular sheet having a length of about 30 mm. The rectangular sheet was stretched using the mechanical apparatus by a further 50 mm so that the new length was 80 mm. The sample was left in the stretched position for 6 minutes and then removed from the apparatus. The sample returned to its original dimensions in about one minute.

Figure 7:
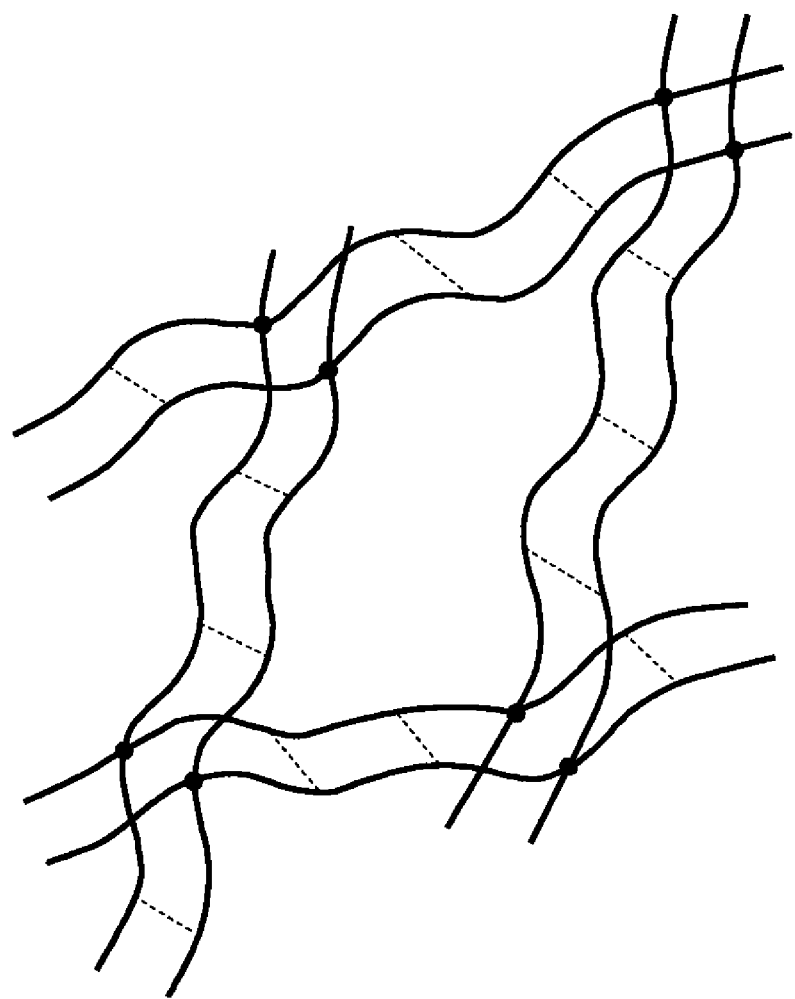
FIG. 7 is a proposed depiction of a polyelectrolyte complex's ladder and network morphology.

Without being held to a particular theory, it is believed that the good damping properties of compacted articles comprising polyelectrolyte complex stem from their unusual internal morphology. It is believed that the electrostatic "crosslinks" between positive and negative polymers comprise both "ladder" and "network" character. See FIG. 7 for a depiction of the proposed networked ladder morphology of the polyelectrolyte complex. In FIG. 7, solid lines represent PSS and PDADMA chains. Dashed lines are ladder-type ion pairs. Solid circles represent a network crosslink.

The proposed depiction of the compacted article as being a tightly crosslinked system comprising an electrostatic crosslink per monomer repeat unit with relatively short molecular chains of reduced flexibility is not entirely accurate, and the ladder character imparts complexes with some flexibility crucial for damping. In the absence of salt, all polymers are ion paired and the polyelectrolyte ladders (and individual polymer segments within the ladder complexes) are essentially frozen. Salt works as a lubricating agent, freeing up frozen polyelectrolyte ladders, similar to the observed softening of brittle glassy polymers when the temperature is raised beyond their glass transition temperature ($T_g$), an analogy that may be termed "counter ion-induced plasticization".

A run of ladder-type ion pairs (as seen in FIG. 7) is like a length of high-mass polymer (the mass is the sum of the two polyelectrolytes involved) that does not interact with its surroundings. Waters of hydration around this run provide opportunities for enhanced molecular motion, further absorbing energy. As ion pairs are broken by the addition of salt, the effective mass of the free runs of paired polyelectrolyte increases, as does the damping effectiveness. The fact that damping is constant over a range of (lower) frequencies is a further advantage of the polyelectrolyte complex system. This behavior is likely due to the statistical distribution of ladder lengths in complexes, with each length of ladder run able to absorb a specific frequency of mechanical energy.

Example 8

Rheometer Studies

The dynamic shear moduli, including the dynamic storage ($G_1$) modulus and the loss ($G_2$) modulus, of the centrifugally compacted article comprising PSS/PDADMA prepared according to the method of Example 5 were tested. The centrifugally compacted PSS/PDADMAC complexes were immersed in solutions of different sodium chloride concentrations (0.0M and 2.5M). The moduli were determined on a controlled stress strain rheometer (Bohlin Gemini, Malvern Instruments) equipped with a parallel plate configuration (diameter=20 mm) in a humidity enclosure chamber. The temperature was controlled to 37.0±0.1° C. using a Peltier plate device. Experimental control and data collection were carried out using a PC-based system and a custom software provided by Bohlin. The samples were first subjected to an oscillation strain sweep at different angular frequencies (1 Hz, 10 Hz, and 30 Hz) to determine the linear viscoelastic domain (LVD). Then, a dynamic angular frequency sweep ($8.10^{-5} \leq f \leq 30$ Hz) was achieved by using a strain value, $\gamma_0$, located for all the frequency range within the LVD.

Example 9

Modulus of PDADMA/PSS Complex

Assuming that the network formed is isotropic with a Poisson ratio of 0.5, E can be obtained from G (using data obtained from Example 8) according to the following:

$E=3G.$

The dynamic storage modulus, $E_1$, and loss modulus, $E_2$, versus frequency were recorded for centrifugally compacted polyelectrolyte complexes annealed in a solution comprising 2.5 M sodium chloride (FIG. 8) and a solution comprising 0.00 M sodium chloride (FIG. 9) using a rheometer.

Figure 8:
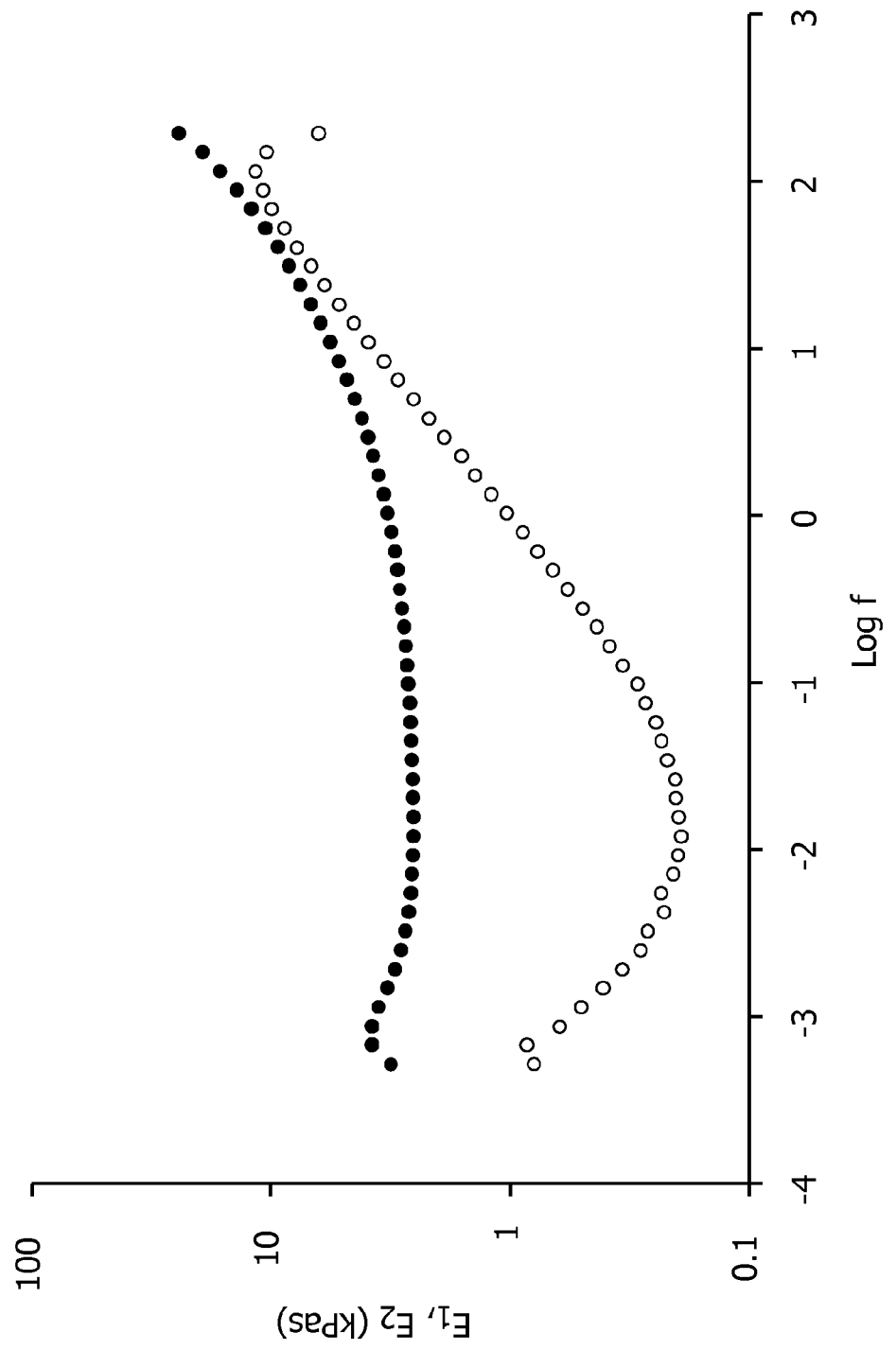
FIG. 8 is a graph showing the dynamic storage modulus, $E_1$, and loss modulus, $E_2$, versus frequency of a compacted article comprising polyelectrolyte complex. The data in the graph were obtained according to the method of Example 9.
Figure 9:
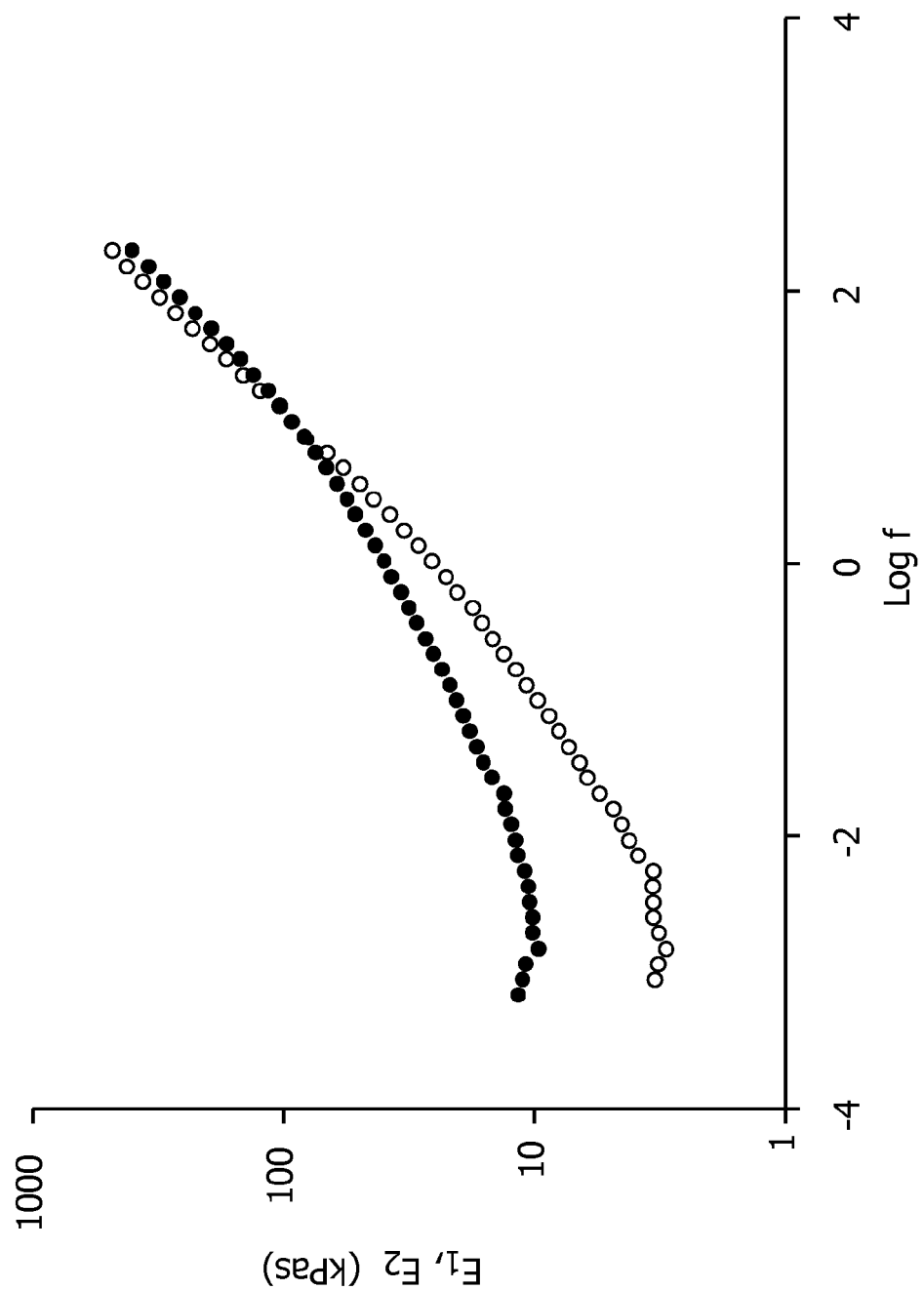
FIG. 9 is a graph showing the dynamic storage modulus, $E_1$, and loss modulus, $E_2$, versus frequency of a compacted article comprising polyelectrolyte complex. The data in the graph were obtained according to the method of Example 9.

In FIGS. 8 and 9, the solid circles represent the dynamic storage modulus data while the open circles represent the loss modulus data.

At low frequencies, the compacted PSS/PDADMAC complexes annealed in water or in 2.50 M NaCl solution exhibited a dominant elastic behavior. $E_1$ has a weak frequency dependence, and it is significantly greater than $E_2$. The plateau value of storage modulus, also called the equilibrium modulus $E_0$, was 3 kPa and 11 kPa for the compacted complexes annealed in 2.50 M and 0.00 M salt, respectively. As previously observed for the polyelectrolyte multilayers, the mechanical properties of the complexes depend on the ionic strength of the solution in which they are immersed. As the salt concentration of the annealing solution (and so in the complexes) increases, the compacted polyelectrolyte complexes are softer and softer (decrease of $E_0$ values).

Figure 10:
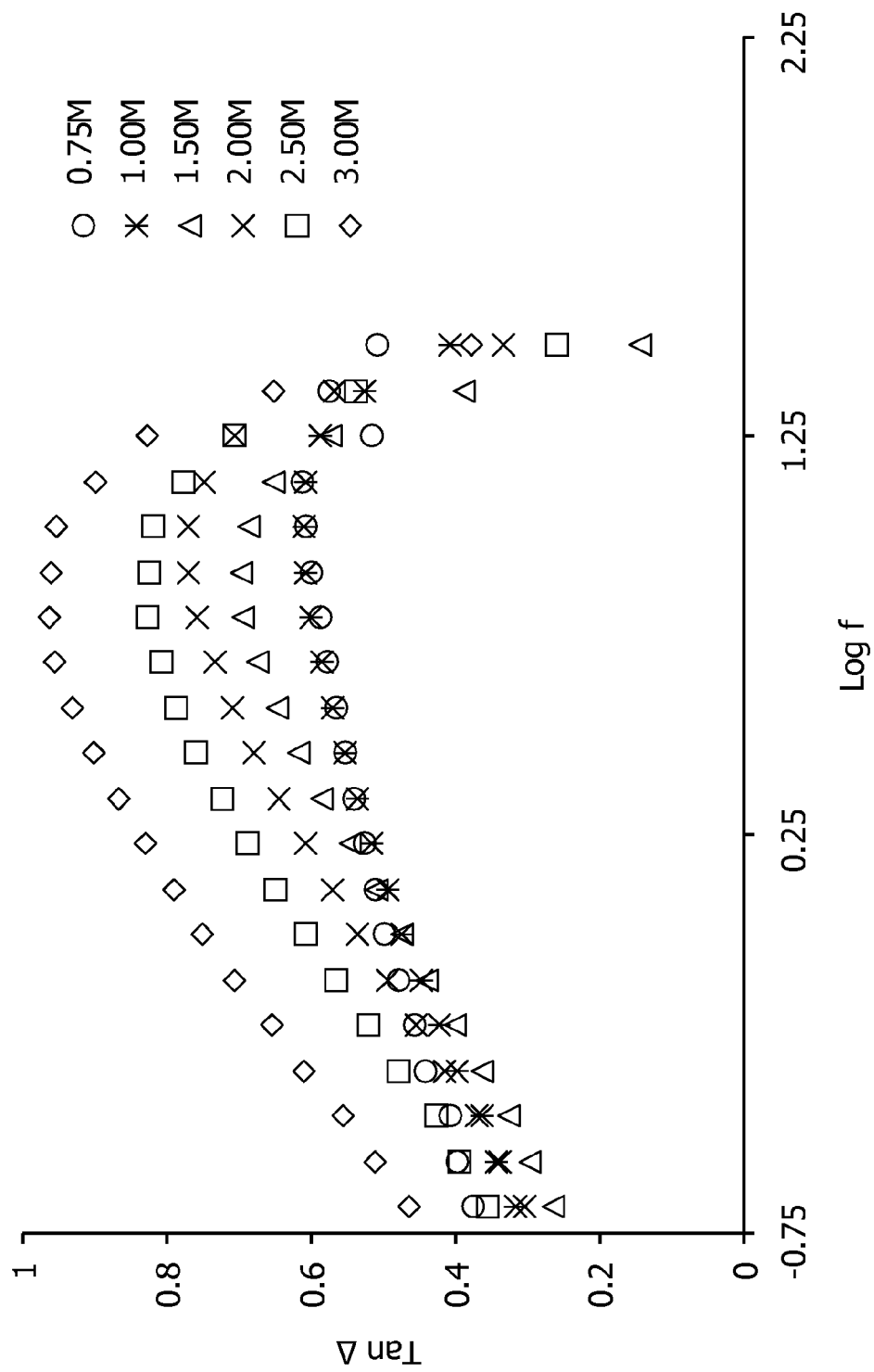
FIG. 10 is a graph showing the damping behavior of a polyelectrolyte complex after conditioning at several ionic strengths. The data in the graph were obtained according to the method of Example 9.

The damping properties of the centrifugally compacted PSS/PDADMAC complexes are similar to those observed in the noncompacted polyelectrolyte complex (Example 4). Δ varies between 16° and 50°. Moreover, between 0.3-30 Hz, Tan(Δ) exhibits not only the same trend observed for the noncompacted polyelectrolyte complexes but also these values lie in the same range. See FIG. 10, which is a graph depicting the damping ability versus frequency at 37° C. In FIG. 10, the curves correspond to salt concentrations as follows: (open circles) 0.75 M NaCl solution; (asterisks) 1.00 M NaCl solution; (open triangles) 1.5 M NaCl solution; (crosses) 2.0 M NaCl solution; (open squares) 2.5 M NaCl solution; (open diamonds) 3.0 M NaCl solution. Solid lines are guides to the eye. The damping ability of the compacted polyelectrolyte complexes is improved as the salt concentration increases.

Centrifugally compacted PSS/PDADMAC complexes having moduli in the kPa range are of widespread interest since many native tissues have moduli in this range. For example in the human intervertebral disks, the nucleus pulposus (~1 kPa) (Iatridis, J. C.; Setton, L. A.; Weidenbaum, M.; Mow, V. C. J. Biomechanics 1997, 30, 1005) and the annulus fibrosis (~100 kPa) (Iatridis, J. C.; Kumar, S.; Foster, R. J.; Weidenbaum, M.; Mow, V. C. J. Ortho. Res. 1999, 17, 732) have moduli in this range.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. An article comprising a polyelectrolyte complex, the polyelectrolyte complex comprising an interior region and a surface stratum, wherein the interior region comprises an intermolecular blend of an interior positively charged polyelectrolyte polymer and an interior negatively charged polyelectrolyte polymer and the surface stratum comprises intermolecular blend of a surface positively charged polyelectrolyte polymer and a surface negatively charged polyelectrolyte polymer, and either or both of the surface positively charged polyelectrolyte polymer and the surface negatively charged polyelectrolyte polymer differ from the interior positively charged polyelectrolyte polymer and the interior negatively charged polyelectrolyte polymer, wherein the article is free of salt crystals having a size greater than about 1 micrometer, and the article has no transverse dimension less than about 10,000 nm.

2. The article of claim 1 wherein the polyelectrolyte complex contains salt ions at a doping level of between about 0.01 and about 0.5.

3. The article of claim 1 wherein the surface stratum comprises a polyelectrolyte polymer comprising fluorinated repeat units.

4. The article of claim 1 wherein the surface stratum comprises a polyelectrolyte polymer comprising zwitterionic repeat units.

5. An article comprising a polyelectrolyte complex, the polyelectrolyte complex comprising an interior region and a surface stratum, wherein the interior region comprises an intermolecular blend of an interior positively charged polyelectrolyte polymer and an interior negatively charged polyelectrolyte polymer and the surface stratum comprises intermolecular blend of an a surface positively charged polyelectrolyte polymer and a surface negatively charged polyelectrolyte polymer, wherein the surface stratum and the interior region have a complex shear modulus and the complex shear modulus of the surface stratum is greater than the complex shear modulus of the interior region, and wherein the article is free of salt crystals having a size greater than about 1 micrometer, and the article has no transverse dimension less than about 10,000 nm.

6. The article of claim 5 wherein the complex shear modulus of the surface stratum is at least two times greater than the complex shear modulus of the interior region.

7. The article of claim 5 wherein the surface stratum comprises cross-linking induced by chemical crosslinking, heat treatment, or photocrosslinking.

8. A method for preparing the article of claim 1 comprising a polyelectrolyte complex, the method comprising:
   combining a predominantly positively-charged polyelectrolyte polymer and a predominantly negatively charged polyelectrolyte polymer in a solution comprising a salt at a salt concentration of at least 0.1 M to about 4 M to form a polyelectrolyte complex having a doping level ratio of at least about 0.01 to 0.50; and
   applying a mechanical force to compact the polyelectrolyte complex in contact with said solution and thereby form an article comprising the compacted polyelectrolyte complex.

9. The method of claim 8 wherein the compacted article has a complex shear modulus between about 1 kPa and about 300 MPa at a frequency between about 0.1 Hz and about 10,000 Hz.

10. The method of claim 8 wherein the compacted article has a loss factor of at least about 0.2 at a frequency between about 0.1 Hz and about 10,000 Hz.

11. The method of claim 8 wherein the solution comprises the salt selected from the group consisting sodium chloride, potassium chloride, magnesium chloride, calcium chloride, aluminum chloride, trisodium citrate, disodium hydrogencitrate, sodium dihydrogencitrate, tripotassium citrate, dipotassium hydrogencitrate, potassium dihydrogencitrate, magnesium citrate, calcium citrate, trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, magnesium phosphate, and combinations thereof.

12. The method of claim 8 wherein the mechanical force is applied by centrifugation having a force of at least about 10,000 g to about 1,000,000 g.

13. The method of claim 12 wherein centrifugation occurs in the presence of a solution having the salt concentration between about 0.1 M and about 5 M.

14. The method of claim 8 wherein the mechanical force is applied by hydrostatic pressure against a filter membrane.

15. The method of claim 8 wherein the compacted polyelectrolyte complex further comprises an additive selected from the group consisting of metallic oxide particles, needle-like clay minerals, carbon-based fibers, and combinations thereof.

16. The method of claim 8 wherein the compacted polyelectrolyte complex further comprises an additive selected from the group consisting of an antibacterial agent, an anti-inflammation agent, an antirejection agent, and any combination thereof.

17. The method of claim 8 wherein the polyelectrolyte complex comprises an interior region and a surface stratum, the interior region comprises an interior positively charged polyelectrolyte polymer and an interior negatively charged polyelectrolyte polymer, the surface stratum comprises a surface positively charged polyelectrolyte polymer and a surface negatively charged polyelectrolyte polymer, and either or both of the surface positively charged polyelectrolyte polymer and the surface negatively charged polyelectrolyte polymer differ from the interior positively charged polyelectrolyte polymer and the interior negatively charged polyelectrolyte polymer.

18. The method of claim 17 wherein the surface stratum is formed in a layer-by-layer buildup method on a surface of the interior region comprising:
   (i) exposing the surface of the interior region to a solution comprising either a positively-charged polyelectrolyte polymer or a negatively-charged polyelectrolyte polymer thereby causing the polyelectrolyte polymer to adsorb thereon;
   (ii) exposing the surface having the polyelectrolyte polymer of step (i) adsorbed thereon to a solution comprising a polyelectrolyte polymer having an overall charge opposite that of the polyelectrolyte polymer of step (i) thereby causing the polyelectrolyte polymer having the overall charge opposite that of the polyelectrolyte polymer of step (i) to adsorb thereon; and
   (iii) repeating steps (i) and (ii) n times to form the surface stratum, where n is from zero to 1000.

19. The method of claim 17 wherein the surface stratum comprises a polyelectrolyte polymer comprising fluorinated repeat units.

20. The method of claim 17 wherein the surface stratum comprises a polyelectrolyte polymer comprising zwitterionic repeat units.

21. The method of claim 17 wherein the surface stratum and the interior region each have complex shear modulus and the complex shear modulus of the surface stratum is greater than the complex shear modulus of the interior region.

22. The method of claim 21 wherein the complex shear modulus of the surface stratum is at least 2 times greater than that of the interior region.

23. The method of claim 21 wherein the surface stratum comprises cross-linking induced by chemical crosslinking, heat treatment, or photocrosslinking.

24. The method of claim 8 wherein the mechanical force is applied through a needle or cannula.

25. The method of claim 8 wherein the article is formed in a cavity.

* * * * *